United States Patent
Ryu et al.

(10) Patent No.: US 11,487,203 B2
(45) Date of Patent: Nov. 1, 2022

(54) MONOMERS, POLYMERS AND PHOTORESIST COMPOSITIONS

(71) Applicant: Rohm and Haas Electronic Materials Korea Ltd., Chungcheongnam-do (KR)

(72) Inventors: Eui Hyun Ryu, Chungcheongnam-Do (KR); Myung-Yeol Kim, Chungcheongnam-Do (KR); Woo-Hyung Lee, Chungcheongnam-Do (KR); Haemi Jeong, Chungcheongnam-do (KR); Kwang-Hwyi Im, Chungcheongnam-do (KR)

(73) Assignee: ROHM AND HAAS ELECTRONIC MATERIALS KOREA LTD., Chungcheongnam-Do (KR)

( * ) Notice: Subject to any disclaimer, the term of this patent is extended or adjusted under 35 U.S.C. 154(b) by 12 days.

(21) Appl. No.: 15/858,129

(22) Filed: Dec. 29, 2017

(65) Prior Publication Data

US 2018/0203352 A1 Jul. 19, 2018

Related U.S. Application Data

(60) Provisional application No. 62/440,802, filed on Dec. 30, 2016.

(51) Int. Cl.

| | | |
|---|---|---|
| *G03F 7/039* | (2006.01) | |
| *G03F 7/38* | (2006.01) | |
| *C08F 220/28* | (2006.01) | |
| *C08F 220/38* | (2006.01) | |
| *C08F 220/68* | (2006.01) | |
| *G03F 7/038* | (2006.01) | |
| *C07C 323/13* | (2006.01) | |
| *C07C 69/54* | (2006.01) | |
| *C08L 33/10* | (2006.01) | |
| *C07D 327/06* | (2006.01) | |
| *C07D 331/00* | (2006.01) | |
| *C07D 327/00* | (2006.01) | |
| *C07D 335/02* | (2006.01) | |
| *C09D 133/06* | (2006.01) | |
| *C07D 307/20* | (2006.01) | |
| *C07C 323/17* | (2006.01) | |
| *C07D 309/10* | (2006.01) | |

(52) U.S. Cl.
CPC ............ *G03F 7/0384* (2013.01); *C07C 69/54* (2013.01); *C07C 323/13* (2013.01); *C07C 323/17* (2013.01); *C07D 307/20* (2013.01); *C07D 309/10* (2013.01); *C07D 327/00* (2013.01); *C07D 327/06* (2013.01); *C07D 331/00* (2013.01); *C07D 335/02* (2013.01); *C08F 220/281* (2020.02); *C08F 220/282* (2020.02); *C08F 220/285* (2020.02); *C08F 220/38* (2013.01); *C08F 220/382* (2020.02); *C08F 220/68* (2013.01); *C08L 33/10* (2013.01); *C09D 133/06* (2013.01); *G03F 7/0392* (2013.01); *G03F 7/0397* (2013.01); *G03F 7/38* (2013.01); *C07C 2601/14* (2017.05)

(58) Field of Classification Search
CPC .. C03F 7/00397; C03F 7/0397; C03F 7/0392; C03F 7/38; C08F 2220/281; C08F 2220/282; C08F 2220/285; C08F 220/38; C08F 2220/382; C08F 220/281; C08F 220/282; C08F 220/285; C08F 220/382; C08F 220/68

See application file for complete search history.

(56) References Cited

U.S. PATENT DOCUMENTS

| | | | |
|---|---|---|---|
| 5,843,624 | A | 12/1998 | Houlihan et al. |
| 6,048,662 | A | 4/2000 | Bruhnke et al. |
| 6,048,664 | A | 4/2000 | Houlihan et al. |
| 6,057,083 | A | 5/2000 | Taylor et al. |
| 6,136,501 | A | 10/2000 | Trefonas, III et al. |
| 7,968,268 | B2 | 6/2011 | Wang |
| 8,206,886 | B2 | 6/2012 | Kodama |
| 8,841,060 | B2 | 9/2014 | Kataoka et al. |
| 8,846,293 | B2 | 9/2014 | Iizuka et al. |
| 2003/0027075 | A1* | 2/2003 | Barclay .............. G03F 7/0382 430/270.1 |
| 2012/0064456 | A1 | 3/2012 | Bae et al. |
| 2012/0251948 | A1 | 10/2012 | Iizuka et al. |
| 2013/0004740 | A1 | 1/2013 | Kataoka et al. |
| 2016/0077429 | A1 | 3/2016 | Masuyama et al. |
| 2016/0090494 | A1* | 3/2016 | Suzuki ..................... B41J 2/02 522/42 |
| 2019/0072851 | A1* | 3/2019 | Tanigaki ................. G03F 7/032 |

FOREIGN PATENT DOCUMENTS

| | | |
|---|---|---|
| EP | 0930542 A1 | 7/1999 |
| EP | 1008913 A1 | 6/2000 |
| JP | 201203138 A | 1/2012 |
| JP | 5572656 B2 | 8/2014 |
| JP | 5618924 B2 | 11/2014 |
| JP | 2015111637 A | 6/2015 |
| JP | 5775804 B2 | 9/2015 |
| WO | 2011111807 A1 | 9/2011 |

* cited by examiner

Primary Examiner — John S Chu
(74) Attorney, Agent, or Firm — Cantor Colburn LLP

(57) ABSTRACT

Monomers and polymers are provided that comprise a carbon alicyclic group or heteroalicyclic group that comprises 1) one or more acid-labile ring substituents and 2) one or more ether or thioether ring substituents. Photoresists that comprise such polymers also are provided.

20 Claims, No Drawings

MONOMERS, POLYMERS AND PHOTORESIST COMPOSITIONS

This application claims the benefit of U.S. Provisional Application 62/440,802 filed on Dec. 30, 2016. The entire contents of U.S. Provisional Application 62/440,802 are incorporated herein by reference in the entirety.

BACKGROUND

The invention relates generally to the manufacture of electronic devices. More specifically, this invention relates to photoresist compositions and to photolithographic processes which allow e formation of fine patterns using a negative tone development process.

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

Considerable effort has been made to extend the practical resolution capabilities of photoresist compositions, including though development of various resist composition materials. See JP2015111637A; US20160077429; WO2011111807A1; JP2012031381A; US20130004740A1; U.S. Pat. No. 8,841,060B2; JP5618924B2; US20120251948A1; U.S. Pat. No. 8,846,293B2; JP5572656B2; JP5775804B2.

Immersion lithography also has been explored to extend photoresist resolution. In immersion lithography, the numerical aperture of the exposure tool lens is increased through use of a fluid to focus more light into the resist film. More particularly, immersion lithography utilizes a relatively high refractive index fluid between the last surface of an imaging device (e.g. ArF stepper) and the first on a wafer or other substrate.

Electronic device manufacturers continually seek increased resolution of a patterned photoresist image. It would be desirable to have new photoresist compositions that could provide enhanced imaging capabilities.

SUMMARY

In one aspect, we now provide new monomer and polymers and photoresists that comprise such polymers.

In preferred aspects, polymers are provided that comprise a repeat unit that comprises a carbon alicyclic group or heteroalicyclic group that comprises 1) one or more acid-labile ring substituents and 2) one or more optionally substituted etherated (ether) or thioetherated (thioether) ring substituents. In certain preferred aspects, 1) the acid-labile ring substituent is an ester group and 2) a carbon ring atom of the carbon alicyclic or heteroalicyclic group is a quaternary carbon of the acid-labile ester group.

Ether ring substituents of a carbon alicyclic group or heteroalicyclic group suitably may be a variety of moieties such as the same or different optionally substituted alkoxy groups including optionally substituted $C_{1-20}$ alkoxy that may comprise 1, 2, 3 or more oxygen atoms such as methoxy (—$OCH_3$); and optionally substituted aryloxy groups such as optionally substituted carbocyclic aryloxy for example optionally substituted phenoxy (—$OC_6H_5$).

Thioether ring substituents of a carbon alicyclic group or heteroalicyclic group suitably may be a variety of moieties such as the same or different optionally substituted thioalkyl groups including optionally substituted $C_{1-20}$ thioalkyl that may comprise 1, 2, 3 or more sulfur atoms such as methylthioether (—$SCH_3$); and optionally substituted arylthioether groups such as optionally substituted carbocyclic arylthioether for example such as optionally substituted phenylthioether (—$SC_6H_5$).

In a preferred aspect, a polymer may comprise a structure of either or both of the following Formulae (I) or (I'):

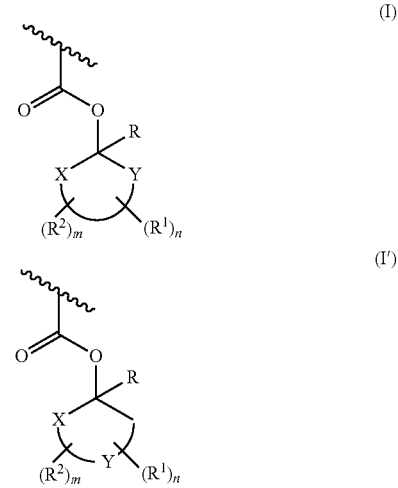

wherein in Formulae (I):

X and Y are independently C, O, or S and form a carbon alicyclic ring or heteroalicyclic ring (a heteroalicyclic ring where one of X or Y is a hetero atoms particularly O or S);

R is a non-hydrogen substituent such optionally substituted alkyl (e.g. optionally substituted $C_{1-20}$ alkyl including cycloalkyl), optionally substituted heteroalkyl (e.g. optionally substituted $C_{1-20}$ alkoxy), and optionally substituted carbocyclic aryl (such as optionally substituted phenyl);

$R^1$ is optionally substituted ether or optionally substituted thioether;

$R^2$ is a non-hydrogen substituent such as alkyl ester (e.g. $C_{1-20}$ alkylester e.g. —$CH_3C(=O)O$—, —$CH_3CH_2C(=O)O$—);

m is an integer an integer of 0 (where no $R^2$ groups are present) or greater;

n is a positive integer (e.g., 1, 2, 3, 4, 5 or 6); and the sum of m and n do not exceed the available valances of the carbon alicyclic ring or heteroalicyclic ring;

wherein in Formulae (I'):

X and Y are independently C, O, or S and form a carbon alicyclic ring or heteroalicyclic ring (a heteroalicyclic ring where one of X or Y is a hetero atoms particularly O or S);

R is a non-hydrogen substituent such optionally substituted alkyl (e.g. optionally substituted $C_{1-20}$ alkyl including cycloalkyl), optionally substituted heteroalkyl (e.g. optionally substituted $C_{1-20}$ alkoxy), and optionally substituted carbocyclic aryl (such as optionally substituted phenyl);

$R^1$ is optionally substituted ether or optionally substituted thioether;

$R^2$ is a non-hydrogen substituent such as alkyl ester (e.g. $C_{1-20}$ alkylester e.g. —$CH_3C(=O)O$—, —$CH_3CH_2C(=O)O$—);

m is an integer an integer of 0 (where no $R^2$ groups are present) or greater;

n is a positive integer (e.g., 1, 2, 3, 4, 5 or 6); and the sum of m and n do not exceed the available valances of the carbon alicyclic ring or heteroalicyclic ring.

In a preferred aspect, a polymer may comprise a structure of the following Formula (IA):

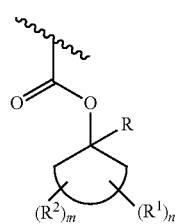

(IA)

wherein in Formula (IA), the depicted cyclic group is a carbon alicyclic group, for example having from 5 to 20 carbon ring atoms, preferably 5 or 6 carbon ring atoms; and R, $R^1$, $R^2$, m and n are the same as defined in Formula (I) above.

In a particularly preferred aspect, a polymer may comprise a structure of the following Formula (II):

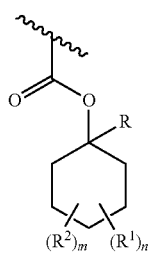

(II)

wherein:

R, $R^1$, $R^2$, m and n are the same as defined in Formula (I) above.

In the Formulae (I), (I'), (IA) and (II) above, the depicted wavy line at the top of the formulae structures represents a chemical bond such as attachment to a group that links to a polymer backbone, or the wavy line depicts a chemical bond or chemical linkage (e.g. —CH$_2$—) that is part of the polymer backbone.

Polymers of the invention may comprise multiple distinct repeat units. Thus, the present polymers may be homopolymers, or more typically will be copolymer, terpolymer, tetrapolymer, pentapolymer or other higher order polymer with 2, 3, 4, 5 or more distinct repeat units. Such additional repeat units need not comprise a structure that comprises a carbon alicyclic group or heteroalicyclic group that comprises 1) one or more acid-labile ring substituents and 2) one or more ether or thioether ring substituents, provided at least one unit of the polymer comprises such a structure with the substituted carbon alicyclic group. The examples below depict preferred additional polymer units.

Particularly preferred polymers of the invention may comprise polymerized acrylate units. In a related embodiment, preferred polymers comprise units obtained by polymerization of one or more monomers of any of the following Formulae (III), (III'), (IIIA), and (IIIB):

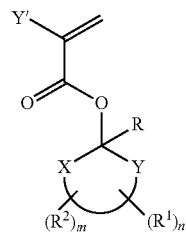

(III)

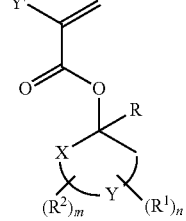

(III')

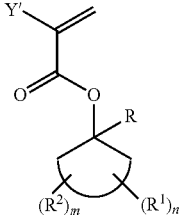

(IIIA)

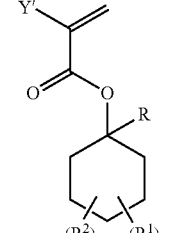

(IIIB)

wherein in Formula (III) and (III'): Y' is hydrogen or optionally substituted alkyl such as optionally substituted $C_{1-6}$ alkyl including methyl; and X, Y, R, $R^1$, $R^2$, m and n are the same as defined in Formula (I).

wherein in Formula (III'): Y' is hydrogen or optionally substituted alkyl such as optionally substituted $C_{1-6}$ alkyl including methyl; and X, Y, R, $R^1$, $R^2$, m and n are the same as defined in Formula (I').

wherein in Formula (IIIA): Y' is hydrogen or optionally substituted alkyl such as optionally substituted $C_{1-6}$ alkyl including methyl; and R, $R^1$, $R^2$, m and n are the same as defined in Formula (IA).

wherein in Formula (IIIB): Y' is hydrogen or optionally substituted alkyl such as optionally substituted $C_{1-6}$ alkyl including methyl; and R, $R^1$, $R^2$, m and n are the same as defined in Formula (II).

Photoresists are also provided that comprise one or more acid generators and one or more polymers as disclosed herein that comprises a structure that comprises a carbon alicyclic group or heteroalicyclic group that comprises 1) one or more acid-labile ring substituents and 2) one or more ether or thioether ring substituents, including a polymer comprising a structure of Formulae (I), (I'), (IA), (II), (III), (III'), (IIIA) and (IIIB) as disclosed above. In preferred aspects, a photoresist of the invention may comprise a second polymer distinct from a polymer that comprises a structure that comprises a carbon alicyclic group or heteroalicyclic group that comprises 1) one or more acid-labile ring substituents and 2) one or more ether or thioether ring substituents. A polymer comprising a carbon alicyclic group or heteroalicyclic group that comprises 1) one or more acid-labile ring substituents and 2) one or more ether or thioether ring substituents (such as a structure of Formulae (I), (I'), (IA), (II), (III), (III'), (IIIA) and (IIIB) above is sometimes referred to herein as a "first polymer" or "primary polymer" of a photoresist composition. In certain preferred aspects, the present photoresists may comprise an additional polymer (sometimes referenced to herein as a "second polymer" of the photoresist composition) which is distinct from the first or primary polymer. The second polymer optionally may comprise acid-labile groups. As further discussed below, in certain embodiments, the first and second polymers may have differing surface energies.

In certain preferred aspects, the first polymer may further comprise third units that (1) comprise one or more hydrophobic groups and (2) repeat units that comprise a structure that comprises a carbon alicyclic group or heteroalicyclic group that comprises 1) one or more acid-labile ring substituents and 2) one or more ether or thioether ring substituents (such as a structure of Formulae (I), (I'), (IA), (II), (III), (III'), (IIIA) and (IIIB) above. Suitably, such one or more hydrophobic groups each comprise 3, 4, 5, 6, 7, 8 or more carbon atoms such as optionally substituted alkyl or alkoxy groups that have such number of carbon atoms.

Methods of processing a photoresist composition are also provided that may suitably comprise applying a layer of a photoresist composition as disclosed herein on a substrate; exposing the photoresist composition layer to activating radiation; and developing the exposed photoresist composition to provide a photoresist relief image. Suitably, the photoresist composition layer may be immersion exposed. Dry (non-immersion) exposure also will be suitable. In certain aspects, implant and EUV lithography processes are also preferred.

In a preferred aspect, unexposed portions of the photoresist layer are removed by the developer, leaving a photoresist pattern over the one or more layer to be patterned. The patternwise exposing can be conducted by immersion lithography or, alternatively, using dry exposure techniques.

According to a further aspect, coated substrates are provided. The coated substrates comprise a substrate and a layer of a photoresist composition of the invention over a surface of the substrate.

Electronic devices formed by the disclosed methods are also provided, including devices formed by the disclosed negative tone development processes.

Monomers are also provided that comprises a structure of a structure that comprises a carbon alicyclic group or heteroalicyclic group that comprises 1) one or more acid-labile ring substituents and 2) one or more ether or thioether ring substituents. Preferred monomers comprise a structure of Formulae (I), (I'), (IA), (II), (III), (III'), (IIIA) and (IIIB) above.

As used herein, the articles "a" and "an" are inclusive of one or more unless otherwise indicated expressly or by context.

Other aspects of the invention are disclosed infra.

DETAILED DESCRIPTION

As discussed above, preferred polymers and monomers may comprise a structure of Formulae (I), (I'), (IA), (II), (III), (III'), (IIIA) and/or (IIIB) as those formulae are set forth above. In those Formulae (I), (I'), (IA), (II), (III), (III'), (IIIA) and/or (IIIB), preferred $R^1$ groups that are optionally substituted ether may be a variety of moieties such as the same or different optionally substituted alkoxy groups including optionally substituted $C_{1-20}$alkoxy that may comprise 1, 2, 3 or more oxygen atoms such as methoxy (—$OCH_3$); and optionally substituted aryloxy groups such as optionally substituted carbocyclic aryloxy for example optionally substituted phenoxy (—$OC_6H_5$). In those Formulae (I), (I'), (IA), (II), (III), (III'), (IIIA) and/or (IIIB), preferred $R^1$ groups that are optionally substituted thioether suitably may be a variety of moieties such as the same or different optionally substituted thioalkyl groups including optionally substituted $C_{1-20}$ thioalkyl that may comprise 1, 2, 3 or more sulfur atoms such as methylthioether (—$SCH_3$); and optionally substituted arylthioether groups such as optionally substituted carbocyclic arylthioether for example optionally substituted phenylthioether (—$SC_6H_5$).

As discussed, in certain preferred aspects, a photoresist of the invention may comprise at least two distinct polymers: 1) a first polymer (primary polymer) that comprises a carbon alicyclic group or heteroalicyclic group that comprises a) one or more acid-labile ring substituents and b) one or more ether or thioether ring substituents (such as a structure of Formula (I), (I'), (IA), (II), (III), (III'), (IIIA) and (IIIB) and 2) a second polymer that is distinct from the first polymer. The second polymer need not contain a carbon alicyclic group or heteroalicyclic group that comprises a) one or more acid-labile ring substituents and b) one or more ether or thioether ring substituents. In preferred compositions, the first or second polymer can migrate toward the upper surface of the resist coating layer during coating of the photoresist composition. In certain systems, this can form a surface layer substantially made up of the migrating first or second polymer. In certain preferred compositions, the second polymer migrates toward the upper surface of the resist coating layer during coating of the photoresist composition. Following exposure and post exposure bake (PEB), the resist coating layer can be developed, including in a developer comprising an organic solvent. If an organic developer is employed, such developer removes unexposed regions of the photoresist layer and the surface layer of the exposed regions. Aqueous alkaline developer also can be utilized that remove exposed regions of a resist coating layer. Benefits of the inventive photoresist compositions can be achieved when using the compositions in dry lithography or immersion lithography processes. When used in immersion lithography, preferred photoresist compositions can further exhibit reduced migration (leaching) of photoresist materials into an immersion fluid also a result of the additive polymer's migration to the resist surface. Significantly, this can be achieved without use of a topcoat layer over the photoresist.

As discussed above, various materials and substituents (including groups of Formulae (I), (I'), (IA), (II), (III), (III'), (IIIA) and (IIIB) which may be "optionally substituted" may be suitably substituted at one or more available positions by e.g. halogen (F, Cl, Br, I); cyano; nitro; hydroxy; amino; alkyl such as $C_{1-20}$ alkyl or $C_{1-8}$ alkyl; alkenyl such as $C_{2-8}$ alkenyl; alkylamino such as $C_{1-20}$ alkylamino or $C_{1-8}$ alkylamino; thioalkyl such as $C_{1-20}$ athioalkyl or $C_{1-8}$ thioalkyl; carbocyclic aryl such as phenyl, naphthyl, anthracenyl, etc; and the like.

The photoresists can be used at a variety of radiation wavelengths, for example, wavelengths of sub-400 nm, sub-300 or sub-200 nm, or with 248 nm, 193 nm and EUV (e.g., 13.5 nm) exposure wavelengths being preferred. The compositions can further be used in electron beam (E-beam)

exposure processes. The photoresist compositions of the invention are preferably chemically-amplified materials.

Preferred monomers (including preferred monomers of Formulae (III), (III'), (IIIA) and/or (IIIB) include the following which can be reacted optionally with one or more other monomers to form a preferred polymer as disclosed herein ((including preferred polymers of Formulae (I), (I'), (IA) and/or (II):

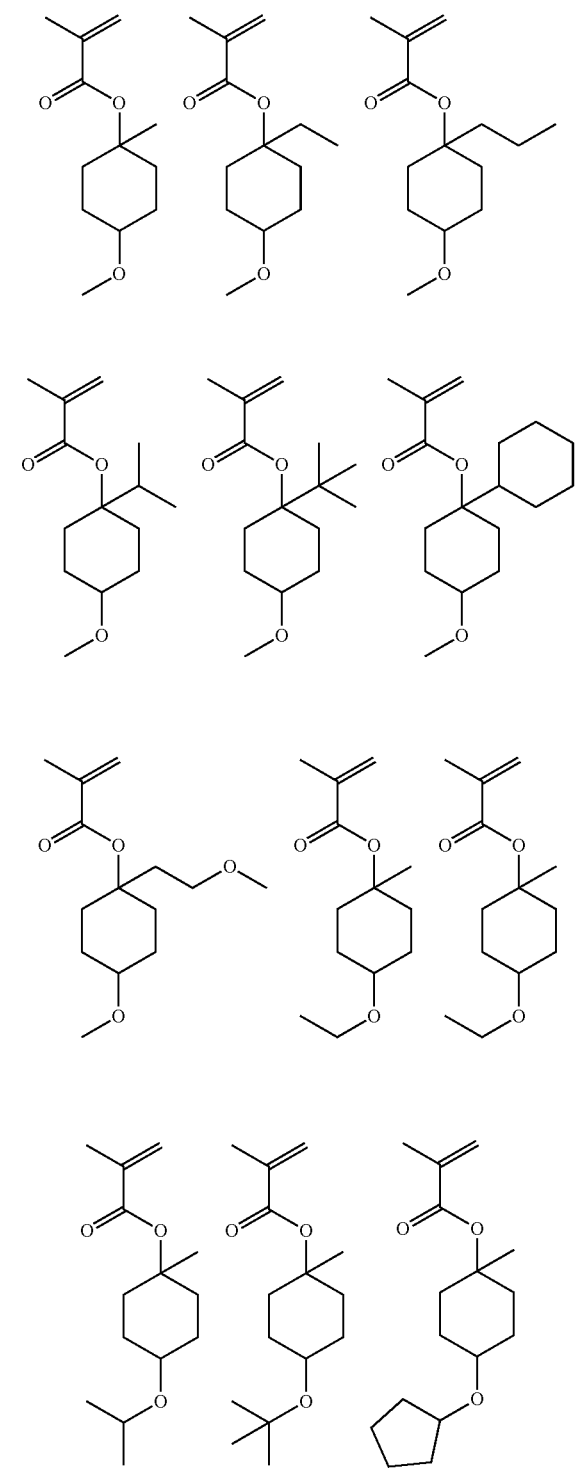
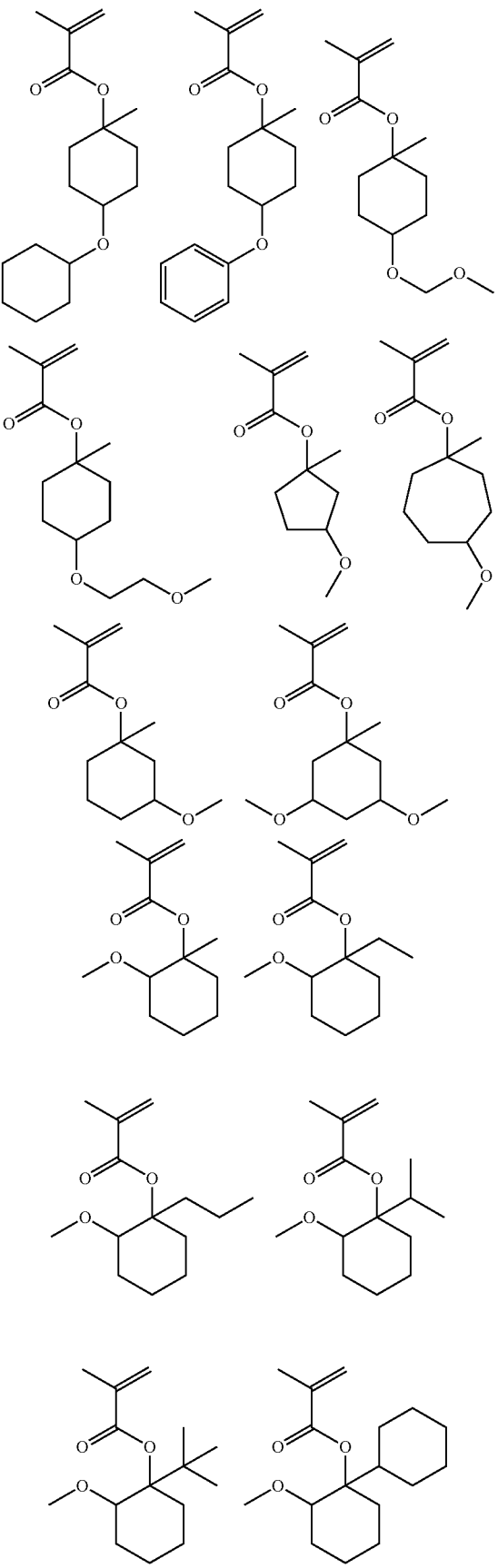

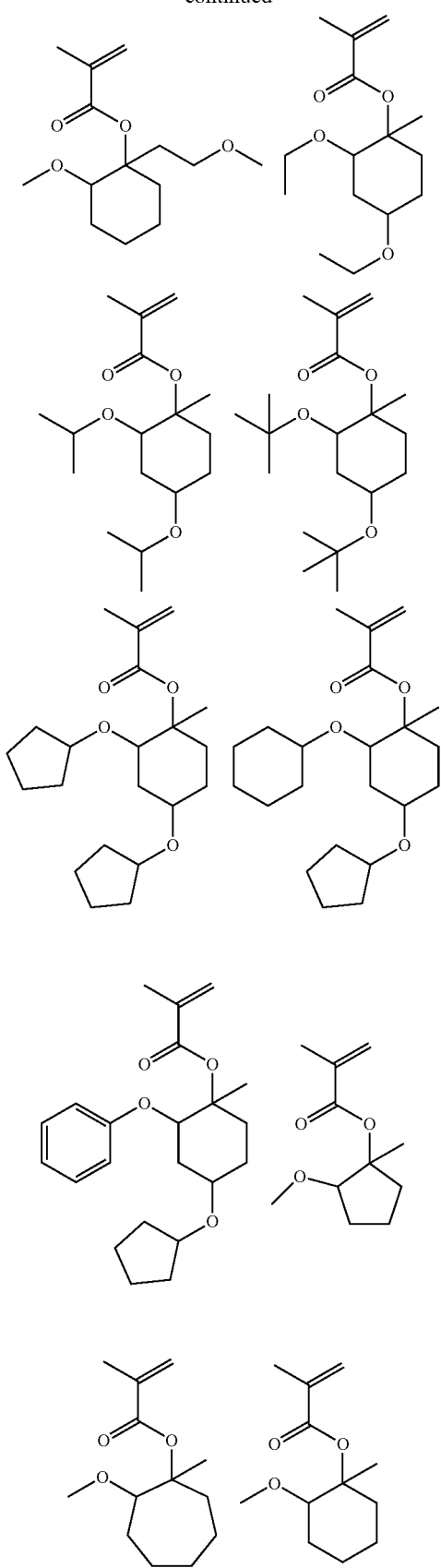
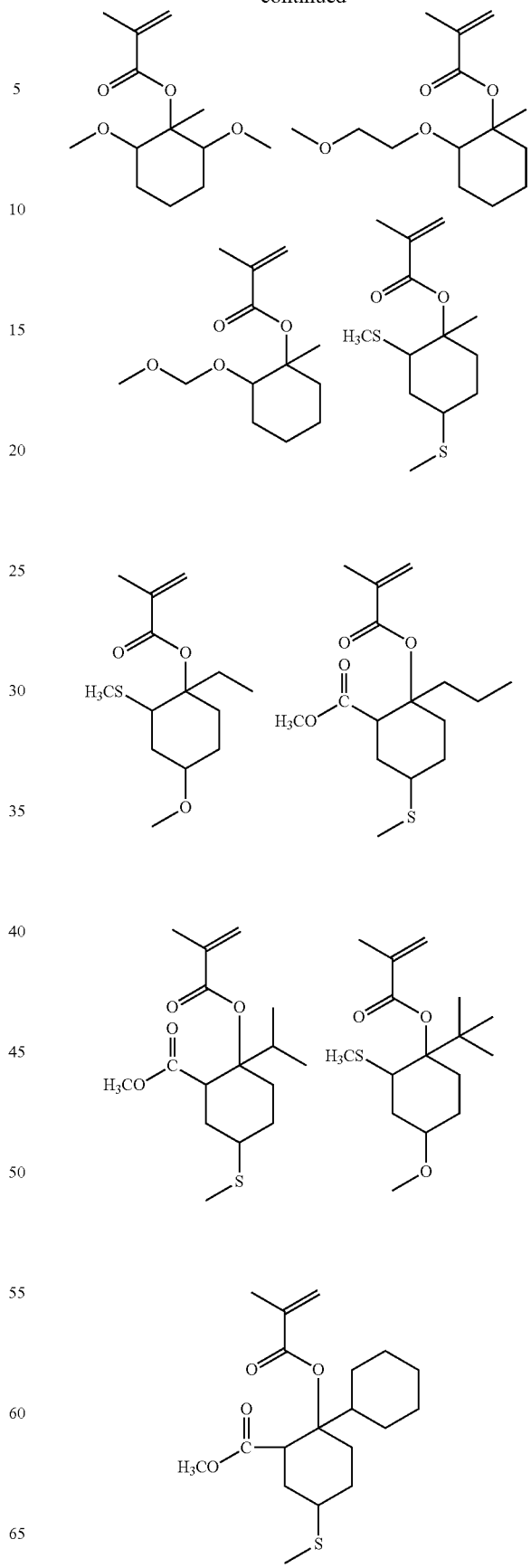

-continued
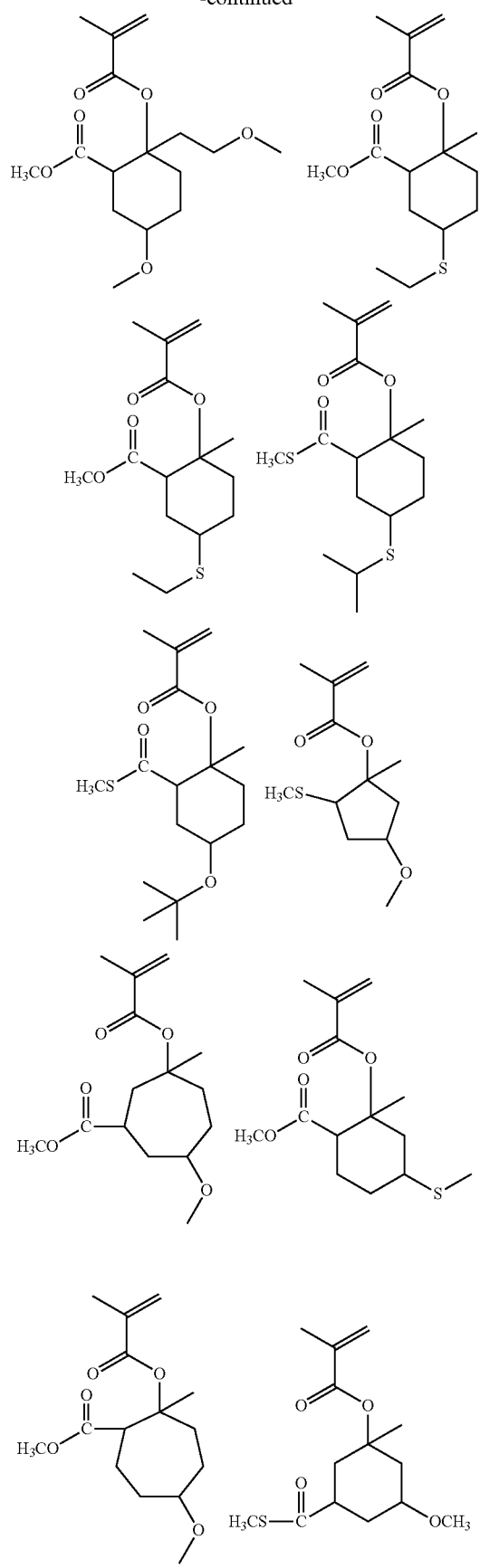
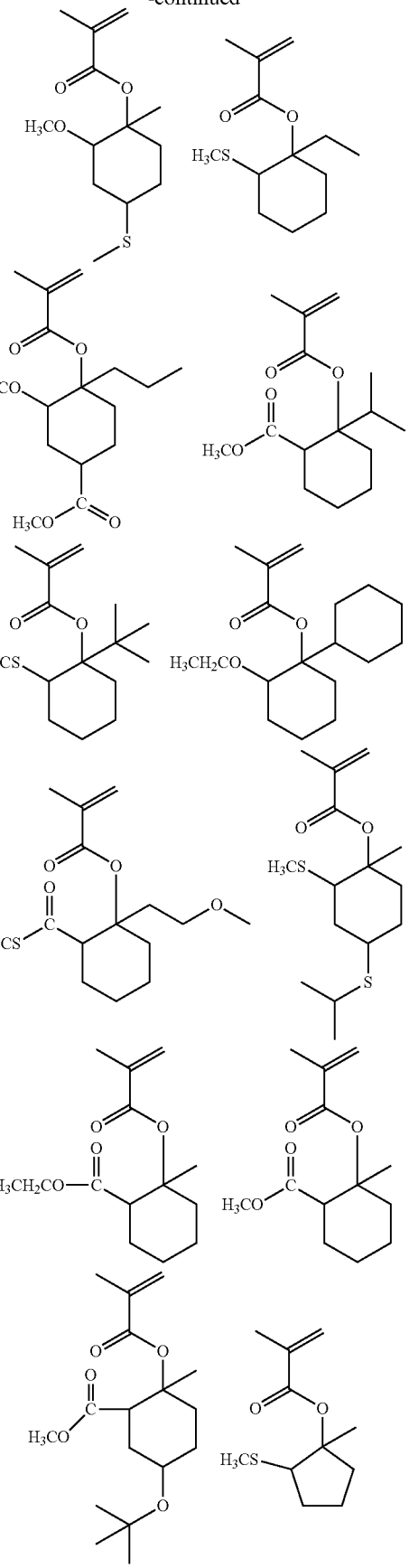

-continued
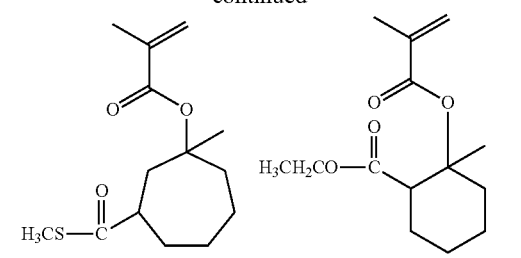
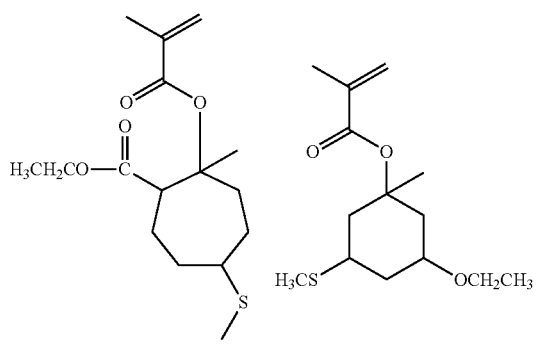
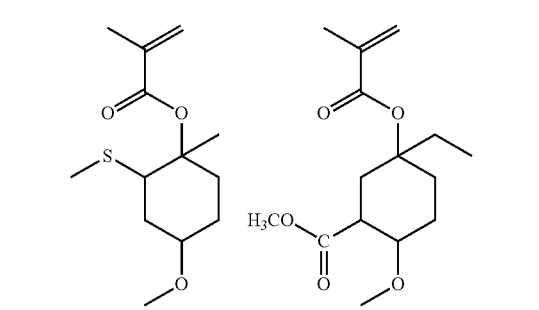
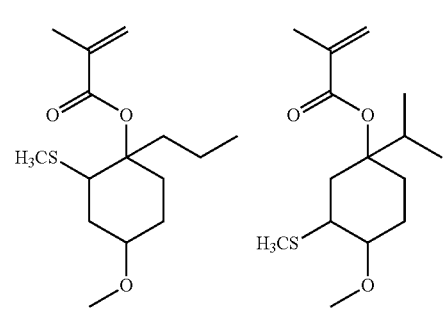
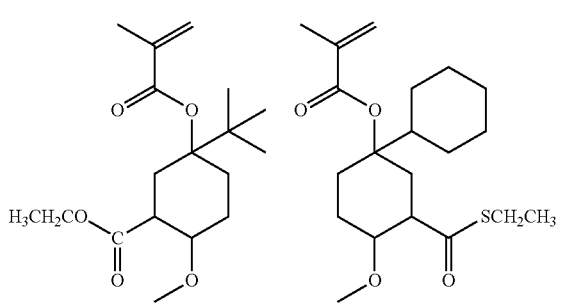
-continued
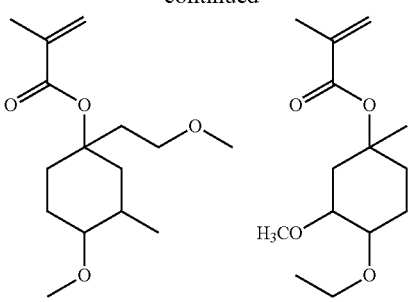
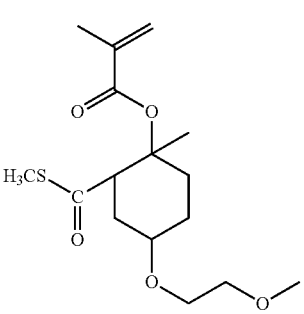

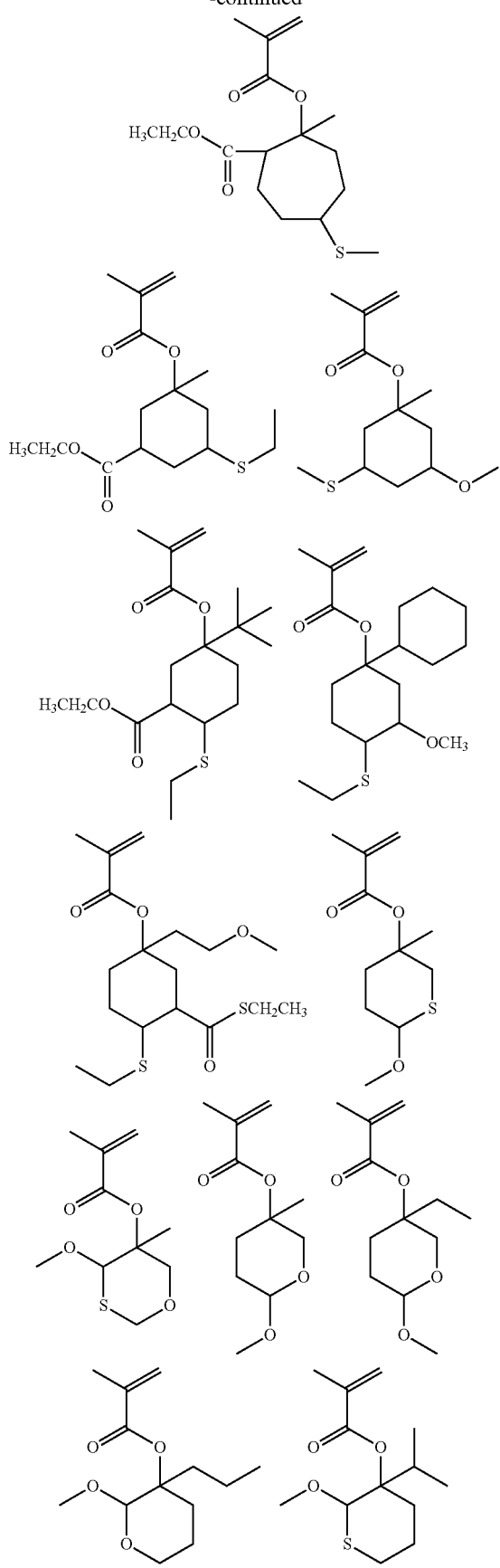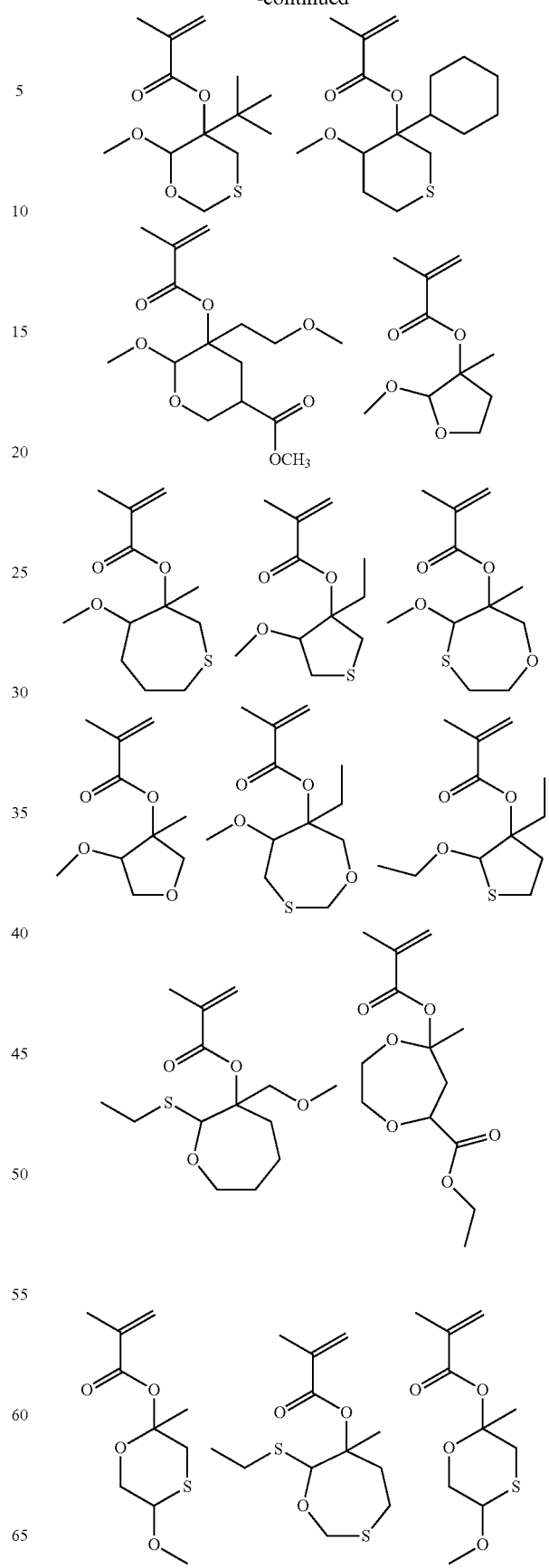

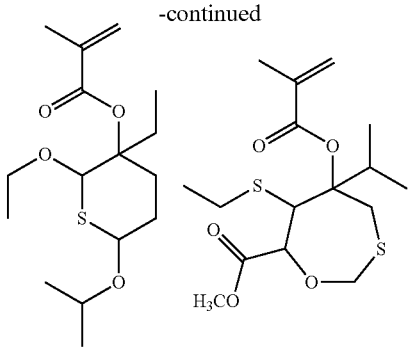

Monomers and polymers can be readily prepared that comprise a carbon alicyclic group or heteroalicyclic group that comprises 1) one or more acid-labile ring substituents and 2) one or more ether or thioether ring substituents. For instance, a carbon alicyclic group or heteroalicyclic group that comprises a ring keto group can be reacted with a Grignard reagent to provide a carbon alicyclic group that has a quaternary ring carbon, where one or such carbon ring atom substituents is a hydroxy moiety. That hydroxyl can be further functionalized as desired such as by reaction with an acyl halide to provide an acrylate monomer. Such monomer can be reacted including with one or more distinct other monomers to prepare a desired polymer. See, for instance, Examples 1 through 7 which follow.

Polymers that comprise a carbon alicyclic group or heteroalicyclic group that comprises 1) one or more acid-labile ring substituents and 2) one or more ether or thioether ring substituents can be reacted with such monomers to provide a homopolymer, or reacted with other distinct compounds to provide a higher order polymer such as a copolymer (at least two distinct repeat units), terpolymer (three distinct repeat units), tetrapolymer (four distinct repeat units), or pentapolymer (five distinct repeat units). An initiator compound can be used as desired. ee Examples 8 through 11 which follow for exemplary preferred syntheses.

In photoresist compositions, in the case of preferred polymers, the polymer repeat unit that that comprises a carbon alicyclic group or heteroalicyclic groups that comprises 1) one or more acid-labile ring substituents and 2) one or more ether or thioether ring substituents can function as an acid labile group and undergo deprotection reaction in the presence of an acid generated from the photoacid and/or thermal acid generator during lithographic processing, particularly following softbake, exposure to activating radiation and post exposure bake. This results from photoacid-induced cleavage of the acid labile group, causing a change in polarity of the polymer.

The polymer also may comprise one or more additional acid labile groups can be chosen, for example, from tertiary alkyl carbonates, tertiary alkyl esters, tertiary alkyl ethers, acetals and ketals. Preferably, the acid labile group is an ester group that contains a tertiary non-cyclic alkyl carbon or a tertiary alicyclic carbon covalently linked to a carboxyl oxygen of an ester of the second matrix polymer. The cleavage of such acid labile groups results in the formation of carboxylic acid groups. Suitable acid labile-group containing units include, for example, acid-labile (alkyl)acrylate units, such as t-butyl (meth)acrylate, 1-methylcyclopentyl (meth)acrylate, 1-ethylcyclopentyl (meth)acrylate, 1-isopropylcyclopentyl (meth)acrylate, 1-propylcyclopentyl (meth) acrylate, 1-methylcyclohexyl (meth)acrylate, 1-ethylcyclohexyl (meth)acrylate, 1-isopropylcyclohexyl (meth)acrylate, 1-propylcyclohexyl (meth)acrylate, t-butyl methyladamantyl(meth)acrylate, ethylfenchyl(meth)acrylate, and the like, and other cyclic, including alicyclic, and non-cyclic (alkyl) acrylates. Acetal and ketal acid labile groups can be substituted for the hydrogen atom at the terminal of an alkali-soluble group such as a carboxyl group or hydroxyl group, so as to be bonded with an oxygen atom. When acid is generated, the acid cleaves the bond between the acetal or ketal group and the oxygen atom to which the acetal-type acid-dissociable, dissolution-inhibiting group is bonded. Exemplary such acid labile groups are described, for example, in U.S. Pat. No. 6,057,083, U.S. Pat. No. 6,136,501 and U.S. Pat. No. 8,206,886 and European Pat. Pub. Nos. EP01008913A1 and EP00930542A1. Also suitable are acetal and ketal groups as part of sugar derivative structures, the cleavage of which would result in the formation of hydroxyl groups, for example, those described in U.S. Patent Application No. US2012/0064456A1.

For use in photoresists imaged at certain sub-200 nm wavelengths such as 193 nm, the polymer that comprises a carbon alicyclic group or heteroalicyclic group that comprises 1) one or more acid-labile ring substituents and 2) one or more ether or thioether ring substituents is typically substantially free (e.g., less than 15 mole %), preferably completely free, of phenyl, benzyl or other aromatic groups where such groups are highly absorbing of the radiation.

The present polymers may comprise a variety of units including, for example, those which contain polymerized units of a non-aromatic cyclic olefin (endocyclic double bond) such as an optionally substituted norbornene, for example, polymers described in U.S. Pat. Nos. 5,843,624 and 6,048,664. Still other suitable polymer units include polymerized anhydride units, particularly polymerized maleic anhydride and/or itaconic anhydride units, such as disclosed in European Published Application EP01008913A1 and U.S. Pat. No. 6,048,662.

In the case of sub-200 nm wavelengths such as 193 nm and EUV (e.g., 13.5 nm), the present polymers may include a unit containing a lactone moiety for controlling the dissolution rate of the polymer and photoresist composition. Suitable monomers for use in the polymer containing a lactone moiety include, for example, the following:

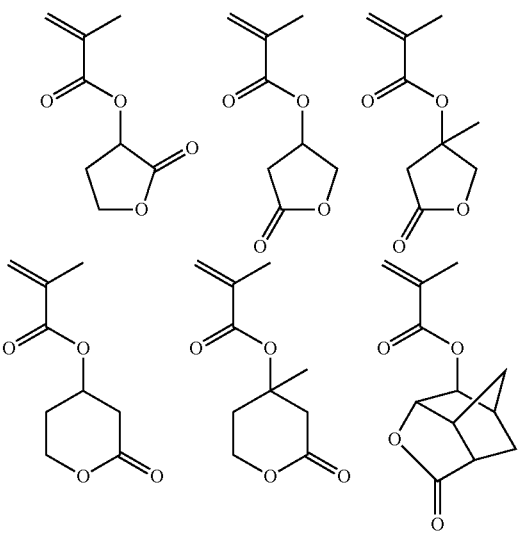

-continued

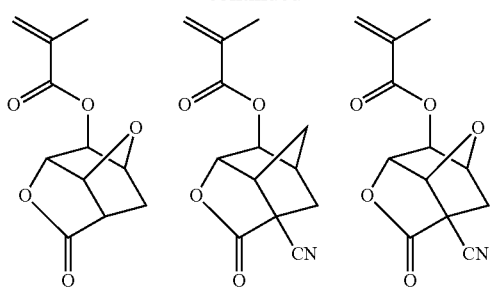

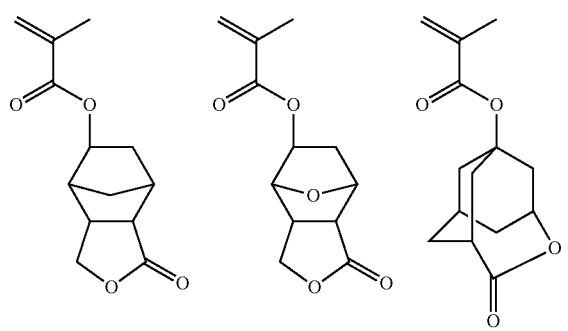

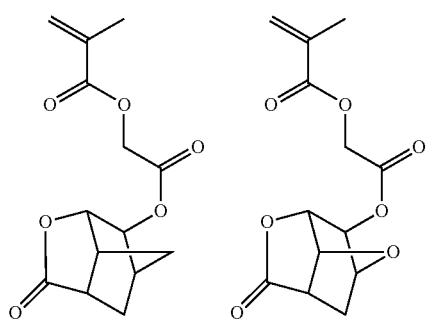

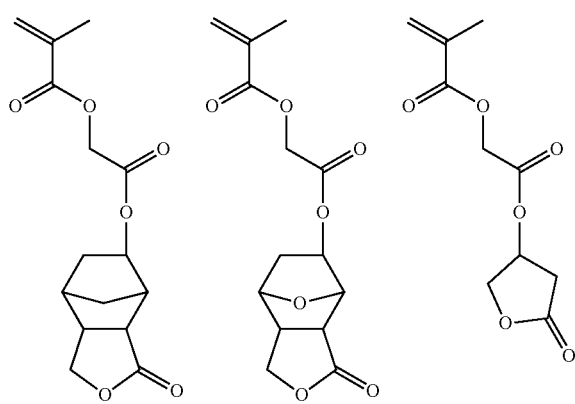

-continued

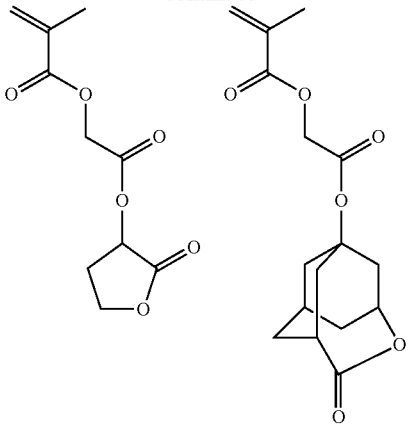

Polymers that comprises a carbon alicyclic group or heteroalicyclic group that comprises 1) one or more acid-labile ring substituents and 2) one or more ether or thioether ring substituents also may contain repeat unit that enhance etch resistance of the polymer and photoresist composition and provides additional means to control the dissolution rate of the polymer and photoresist composition. Monomers for forming such a unit include, for example, the those with additional carbon alicyclic groups, including bridged or multicyclic groups such as following:

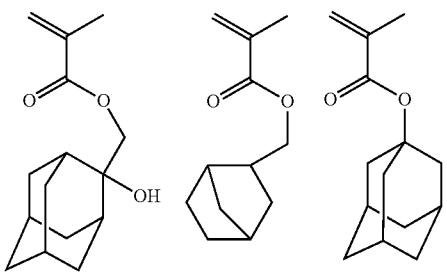

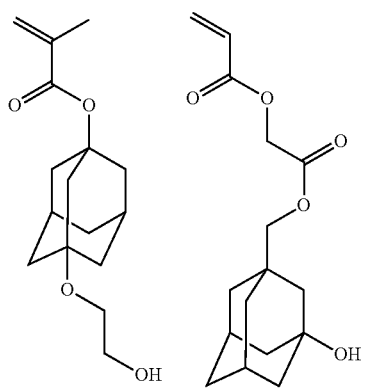

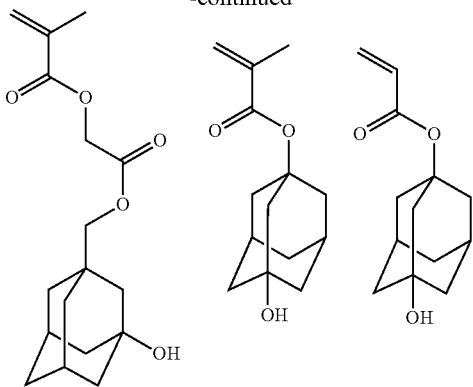

In preferred aspects, the polymer that comprises a carbon alicyclic group or heteroalicyclic group that comprises 1) one or more acid-labile ring substituents and 2) one or more ether or thioether ring substituents has a higher surface energy than that of the first or additive polymer, described below, and should be substantially non-miscible with the first polymer. As a result of the difference in surface energies, segregation of the polymer from the first polymer can take place during spin-coating. A suitable surface energy of the second or matrix polymer is typically from 20 to 50 mN/m, preferably from 30 to 40 mN/m.

A polymer that comprises a carbon alicyclic group or heteroalicyclic group that comprises 1) one or more acid-labile ring substituents and 2) one or more ether or thioether ring substituents is present in the resist composition in an amount sufficient to render an exposed coating layer of the resist developable in a suitable developer solution. Typically, the polymer is present in the composition in an amount of from 50 to 95 wt % based on total solids of the resist composition. The weight average molecular weight $M_w$ of the polymer is typically less than 100,000, for example, from 3000 to 100,000, more typically from 3000 to 15,000. Blends of two or more of the above-described polymers can suitably be used in the photoresist compositions of the invention.

A first polymer that may be additionally employed in a photoresist composition is preferably a material that has a lower surface energy than that of the polymer that comprises a carbon alicyclic group or heteroalicyclic group that comprises 1) one or more acid-labile ring substituents and 2) one or more ether or thioether ring substituents and preferably is substantially non-miscible with the second polymer. In this way, segregation or migration of the first polymer to the top or upper portions of an applied photoresist layer during the coating process is facilitated. While the desired surface energy of the first polymer will depend on the particular primary polymer and its surface energy, the first polymer surface energy is typically from 18 to 40 mN/m, preferably from 20 to 35 mN/m and more preferably from 29 to 33 mN/m. While the first polymer migrates to the upper surface of the resist layer during the coating process, it is preferable that there be some intermixing between the first polymer and primary polymer immediately beneath the resist layer surface. Such intermixing is believed to aid in reducing surface inhibition in the resist layer by reduction or elimination of the acid generated in dark regions in the vicinity of the second or matrix polymer due to stray light. The extent of intermixing will depend, for example, on the difference in surface energy (SE) between the primary polymer and first or additive polymer (AP) ($\Delta SE = SE_{MP} - SE_{AP}$). For given first or primary polymers, the degree of intermixing can be increased with reduced $\Delta SE$. The $\Delta SE$ is typically from 2 to 32 mN/m, preferably from 5 to 15 mN/m.

The first polymer is preferably free of silicon. Silicon-containing polymers exhibit a significantly lower etch rate than organic photoresist polymers in certain etchants. As a result, aggregation of a silicon-containing first polymer at the surface of an organic second polymer-based resist layer can cause cone defects during the etching process. The first polymer may contain fluorine or can be free of fluorine. Preferred first polymers are soluble in the same organic solvent(s) used to formulate the photoresist composition. Preferred first polymers also will be soluble or become soluble upon post exposure bake (e.g., 120° C. for 60 seconds) in organic developers used in negative tone development processes.

Suitable first polymers are disclosed in U.S. Pat. No. 7,968,268, but will preferably comprise a carbon alicyclic group or heteroalicyclic group that comprises 1) one or more acid-labile ring substituents and 2) one or more ether or thioether ring substituents. See also the examples which follow for preferred polymers that can be utilized as a first or primary polymer in a multiple-polymer photoresist composition particularly useful for immersion lithography.

The present photoresist compositions preferably may comprise one or more photoacid generators (PAG) employed in an amount sufficient to generate a latent image in a coating layer of the photoresist composition upon exposure to activating radiation. For example, the photoacid generator will suitably be present in an amount of from about 1 to 20 wt % based on total solids of the photoresist composition. Typically, lesser amounts of the photoactive component will be suitable for chemically amplified resists.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenensulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. One or more of such PAGs can be used.

Suitable solvents for the photoresist compositions of the invention include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

Other optional additives for the photoresist compositions include, for example, actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition, although fillers and dyes can be present in relatively large concentrations, for example, from 5 to 30 wt % based on total solids of the photoresist composition.

A preferred optional additive of resist compositions of the invention is an added base which can enhance resolution of a developed resist relief image. Suitable basic quenchers include, for example: linear and cyclic amides and derivatives thereof such as N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate; aromatic amines such as pyridine, and di-tert-butyl pyridine; aliphatic amines such as triisopropanolamine, n-tert-butyldiethanolamine, tris(2-acetoxy-ethyl) amine, 2,2',2'',2'''-(ethane-1,2-diylbis(azanetriyl))tetraethanol, and 2-(dibutylamino)ethanol, 2,2',2''-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate and N (2-acetoxy-ethyl) morpholine. Of these basic quenchers, 1-(tert-butoxycarbonyl)-4-hydroxypiperidine and triisopropanolamine are preferred. The added base is suitably used in relatively small amounts, for example, from 1 to 20 wt % relative to the PAG, more typically from 5 to 15 wt % relative to the PAG.

The photoresists used in accordance with the invention are generally prepared following known procedures. For example, a resist of the invention can be prepared as a coating composition by dissolving the components of the photoresist in a suitable solvent, for example, one or more of: a glycol ether such as 2-methoxyethyl ether (diglyme), ethylene glycol monomethyl ether, propylene glycol monomethyl ether; propylene glycol monomethyl ether acetate; lactates such as ethyl lactate or methyl lactate, with ethyl lactate being preferred; propionates, particularly methyl propionate, ethyl propionate and ethyl ethoxy propionate; a Cellosolve ester such as methyl Cellosolve acetate; an aromatic hydrocarbon such toluene or xylene; or a ketone such as methylethyl ketone, cyclohexanone and 2-heptanone. The desired total solids content of the photoresist will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

The invention further provides methods for forming a photoresist relief image and producing an electronic device using photoresists of the invention. The invention also provides novel articles of manufacture comprising substrates coated with a photoresist composition of the invention.

In lithographic processing, a photoresist composition may be applied on a variety of substrates. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned may be provided over the substrate. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layers to be etched 102 will vary depending on the materials and particular devices being formed.

Depending on the particular layers to be etched, film thicknesses and photolithographic materials and process to be used, it may be desired to dispose over the layers a hard mask layer and/or a bottom antireflective coating (BARC) over which a photoresist layer is to be coated. Use of a hard mask layer may be desired, for example, with very thin resist layers, where the layers to be etched require a significant etching depth, and/or where the particular etchant has poor resist selectivity. Where a hard mask layer is used, the resist patterns to be formed can be transferred to the hard mask layer which, in turn, can be used as a mask for etching the underlying layers. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer can include a single layer or a plurality of layers of different materials. The hard mask layer can be formed, for example, by chemical or physical vapor deposition techniques.

A bottom antireflective coating may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist layer formed from a composition of the invention as described above is applied on the substrate. The photoresist composition is typically applied to the substrate by spin-coating. During spin-coating, in resist compositions comprising both first and second polymers as disclosed herein, the first polymer in the photoresist segregates to the upper surface of the formed resist layer typically with intermixing with the second polymer in regions immediately below the upper surface. The solids content of the coating solution can be adjusted to provide a desired film thickness based upon the specific coating equipment utilized, the viscosity of the solution, the speed of the coating tool and the amount of time allowed for spinning. A typical thickness for the photoresist layer is from about 500 to 3000 Å.

The photoresist layer can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer is next suitably exposed to activating radiation through a photomask to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions corresponding to regions of the resist layer to remain and be removed, respectively, in a subsequent development step. The exposure wavelength is typically sub-400 nm, sub-300 nm or sub-200 nm, with 248 nm, 193 nm and EUV wavelengths being typical. Photoresist materials can further be used with electron beam exposure. The methods find use in immersion or dry (non-immersion) lithography techniques. The exposure energy is typically from about 10 to 80 mJ/cm$^2$, dependent upon the exposure tool and the components of the photosensitive composition.

Following exposure of the photoresist layer, a post-exposure bake (PEB) is performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds. A latent image defined by the boundary (dashed line) between polarity-switched and unswitched regions (corresponding to exposed and unexposed regions, respectively) is formed in the photoresist. The basic moiety (e.g. amine) of the first polymer deprotected during the post-exppsire bake is believed to prevent polarity switch in dark regions of the photoresist layer where stray or scattered light may be present, resulting in a latent image with vertical walls. This is a result of neutralization of acid generated by the PAG in the dark regions. As a result, cleavage of the acid-labile groups in those regions can be substantially prevented.

The exposed photoresist layer is next developed suitably to remove unexposed regions of the photoresist layer. An aqueous alkaline developer such as alkylammonium aqueous developer may be employed. Also, the developer may be an organic developer, for example, a solvent chosen from ketones, esters, ethers, hydrocarbons, and mixtures thereof. Suitable ketone solvents include, for example, acetone, 2-hexanone, 5-methyl-2-hexanone, 2-heptanone, 4-heptanone, 1-octanone, 2-octanone, 1-nonanone, 2-nonanone, diisobutyl ketone, cyclohexanone, methylcyclohexanone, phenylacetone, methyl ethyl ketone and methyl isobutyl ketone. Suitable ester solvents include, for example, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate and propyl lactate. Suitable ether solvents include, for example, dioxane, tetrahydrofuran and glycol ether solvents, for example, ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol. Suitable amide solvents include, for example, N-methyl-2-pyrrolidone, N,N-dimethylacetamide and N,N-dimethylformamide. Suitable hydrocarbon solvents include, for example, aromatic hydrocarbon solvents such as toluene and xylene. In addition, mixtures of these solvents, or one or more of the listed solvents mixed with a solvent other than those described above or mixed with water can be used. Other suitable solvents include those used in the photoresist composition. The developer is preferably 2-heptanone or a butyl acetate such as n-butyl acetate.

The developer is typically applied to the substrate by spin-coating. The development time is for a period effective to remove the unexposed regions of the photoresist, with a time of from 5 to 30 seconds being typical. Development is typically conducted at room temperature. The development process can be conducted without use of a cleaning rinse following development. In this regard, it has been found that the development process can result in a residue-free wafer surface rendering such extra rinse step unnecessary.

The BARC layer, if present, is selectively etched using resist pattern as an etch mask, exposing the underlying hardmask layer. The hardmask layer is next selectively etched, again using the resist pattern as an etch mask, resulting in patterned BARC and hardmask layers. Suitable etching techniques and chemistries for etching the BARC layer and hardmask layer are known in the art and will depend, for example, on the particular materials of these layers. Dry-etching processes such as reactive ion etching are typical. The resist pattern and patterned BARC layer are next removed from the substrate using known techniques, for example, oxygen plasma ashing.

The following non-limiting examples are illustrative of the invention.
The following non-limiting examples are illustrative of the invention.

Examples 1-7: Synthesis of Monomers

Example 1: Synthesis of
1-ethyl-4-methoxycyclohexyl methacrylate
(EMCHMA)

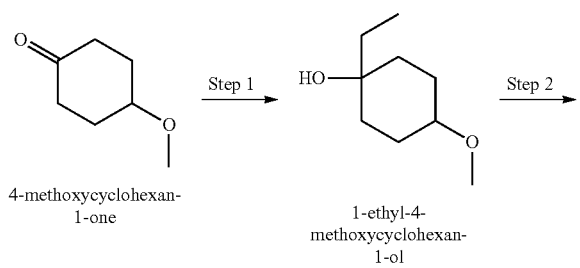

4-methoxycyclohexan-1-one 1-ethyl-4-methoxycyclohexan-1-ol

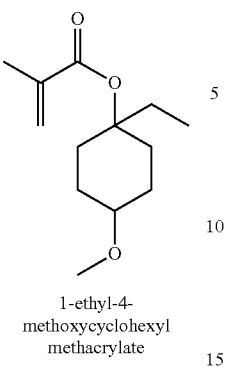

1-ethyl-4-methoxycyclohexyl methacrylate

Step 1. A 36 ml of EtMgBr solution (3M in diethyl ether) was added to 100 ml of anhydrous toluene in 500 ml of round bottom flask A. A 12.6 g of 4-methoxycyclohexan-1-one was dissolved in 13 ml of THF. Prepared THF solution was added to round bottom flask A dropwise over 1 h at 0° C. Reaction mixture was stirred at 0° C. for 2 hours. 50 ml of aqueous NH$_4$Cl was added to flask A slowly. Reaction mixture was extracted with CH$_2$Cl$_2$. Extracted organic phases was dried with Na$_2$SO$_4$ and evaporated in vacuo. The crude product was purified by column chromatography to get final product, 1-ethyl-4-methoxycyclohexan-1-ol with 52% yield (8.24 g). $^1$H NMR (600 MHz, CDCl$_3$): δ (ppm) 3.39 (m, 0.4H), 3.36~3.31 (m, 3H), 3.13 (M, 0.6H), 1.82 (m, 2H), 1.82~1.60 (m, 5H), 1.55~1.45 (m, 2H), 1.40~1.30 (m, 2H), 0.93 (t, 3H).

Step 2. A 8.24 g of 1-ethyl-4-methoxycyclohexan-1-ol was dissolved in 103 ml of CH$_2$Cl$_2$. A 15.88 ml of TEA was added directly. A 6.01 ml of methacryloyl chloride was added slowly at 0° C. and stirred at room temperature for 4 hours. 20 ml of water and 20 ml of aqueous HCl solution (6N) were added consecutively. Reaction mixture was extracted with 100 ml of MC. Collected organic layer was neutralized with 100 ml of aqueous NaHCO$_3$ twice, dried with Na$_2$SO$_4$, and evaporated in vacuo. The crude product was purified by column chromatography to get final product, 1-ethyl-4-methoxycyclohexyl methacrylate (EMCHMA) with 60% yield (7.08 g). $^1$H NMR (600 MHz, CDCl$_3$): δ 6.06-6.04 (m, 1H), 5.50 (s, 1H), 3.42 (m, 0.4H), 3.35~3.31 (m, 3H), 3.18 (M, 0.6H), 2.42 (m, 1H), 2.09 (m, 1H), 1.96~1.90 (m, 6H), 1.68~1.57 (m, 6H), 1.45 (m, 1H), 1.32 (m, 1H), 1.29 (m, 1H), 0.85 (t, 3H).

Example 2: Synthesis of 4-methoxy-1-methylcyclohexyl methacrylate (MMCHMA)

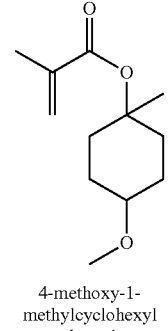

4-methoxy-1-methylcyclohexyl methacrylate

Step 1. A 48 ml of MeMgBr solution (3M in diethyl ether) was added to 140 ml of anhydrous toluene in 500 ml of round bottom flask A. A 17.0 g of 4-methoxycyclohexan-1-one was dissolved in 30 ml of THF. Prepared THF solution was added to round bottom flask A dropwise over 1 h at 0° C. Reaction mixture was stirred at 0° C. for 2 hours. A 110 ml of aqueous NH$_4$Cl was added to flask A slowly. Reaction mixture was extracted with CH$_2$Cl$_2$. Extracted organic phases was dried with Na$_2$SO$_4$ and evaporated in vacuo. The crude product was purified by column chromatography to get final product, 4-methoxy-1-methylcyclohexan-1-ol with 71% yield (13.7 g). $^1$H NMR (600 MHz, CDCl$_3$): δ (ppm) 3.35 (m, 2H), 3.32 (s, 1.43H), 3.13 (m, 0.5H), 1.82 (m, 2H), 1.70 (m, 2H), 1.61 (m, 2H), 1.44 (m, 2H), 1.16 (d, 3H).

Step 2. A 13.7 g of 4-methoxy-1-methylcyclohexan-1-ol was dissolved in 200 ml of CH$_2$Cl$_2$. A 28.9 ml of TEA was added directly. A 11.13 ml of methacryloyl chloride was added slowly at 0° C. and stirred at room temperature for 16 hours. A 150 ml of water, 50 ml of aqueous NH$_4$Cl, and 20 ml of aqueous HCl solution (6N) were added consecutively. Reaction mixture was extracted with 200 ml of MC. Collected organic layer was neutralized with 100 ml of aqueous NaHCO$_3$ twice, dried with Na$_2$SO$_4$, filtered, and evaporated in vacuo. The crude product was purified by column chromatography to get final product, 4-methoxy-1-methylcyclohexyl methacrylate (MMCHMA), with 73% yield. $^1$H NMR (600 MHz, CDCl$_3$): δ 6.05~6.03 (m, 1H), 5.50 (s, 1H), 3.41 (m, 0.44H), 3.35~3.31 (m, 3H), 3.18 (M, 0.56H), 2.39 (m, 1H), 2.06 (m, 1H), 1.92 (s, 3H), 1.86 (m, 1H), 1.80~1.55 (m, 3H), 1.53 (s, 3H), 1.47 (m, 1H), 1.45 (m, 3H).

Example 3: Synthesis of 1-ethyl-cyclohexyl methacrylate (ECHMA)

4-methoxycyclohexan-1-one, 1-ethyl-cyclohexyl methacrylate (ECHMA), was synthesized with the similar procedures with step 2 of Example 1.

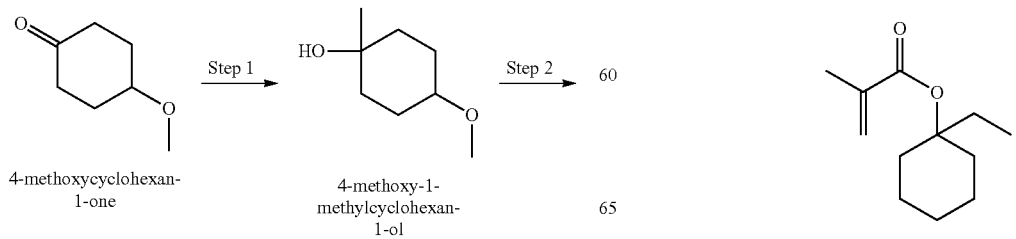

Example 4: Synthesis of 1-methylcyclohexyl methacrylate (MCHMA)

4-Methoxycyclohexan-1-one, 1-methylcyclohexyl methacrylate (MCHMA), was synthesized with the similar procedures with step 2 of Example 1.

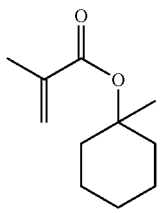

Example 5: Synthesis of 3-ethyl-6-methoxytetrahydro-2H-pyran-3-yl methacrylate

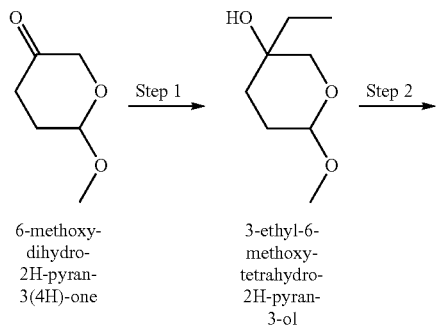

6-methoxy-dihydro-2H-pyran-3(4H)-one → 3-ethyl-6-methoxy-tetrahydro-2H-pyran-3-ol

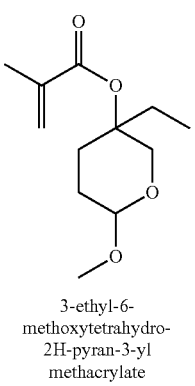

3-ethyl-6-methoxytetrahydro-2H-pyran-3-yl methacrylate

By following the procedures of Example 1 above, but substituting 6-methoxydihydro-2H-pyran-3(4H)-one for 4-methoxycyclohexan-1one, the title compound 3-ethyl-6-methoxytetrahydro-2H-pyran-3-yl methacrylate is prepared.

Example 6: Synthesis of 3-ethyl-6-methoxytetrahydro-2H-thiopyran-3-yl methacrylate

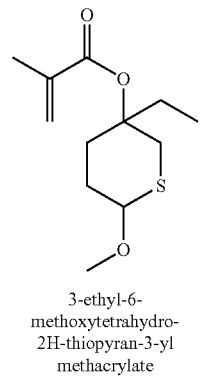

6-methoxy-dihydro-2H-thiopyran-3(4H)-one → 3-ethyl-6-methoxy-tetrahydro-2H-thiopyran-3-ol 3-ethyl-6-methoxytetrahydro-2H-thiopyran-3-yl methacrylate By following the procedures of Example 1 above, but substituting 6-methoxydihydro-2H-thiopyran-3(4H)-one for 4-methoxycyclohexan-1-one, the title compound 3-ethyl-6-methoxytetrahydro-2H-thiopyran-3-yl methacrylate is prepared.

Example 7

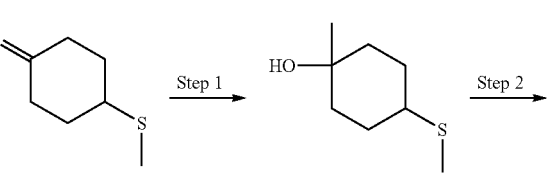

4-(methylthio)-cyclohexan-1-one → 1-methyl-4-(methylthio)-cyclohexan-1-ol

-continued

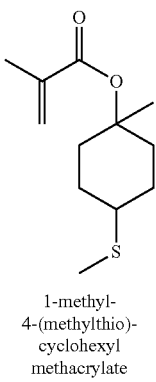

1-methyl-4-(methylthio)-cyclohexyl methacrylate

By following the procedures of Example 1 above, but substituting 6-methylthiocyclohexan-1-one for 4-methoxycyclohexan-1-one, the title compound 4-methylthio-1-methylcyclohezxylmethacrylate is prepared.

Examples 8-11: Polymer Synthesis

General Polymerization Procedures Shown in Example 8 to 11

A series of monomers with different amounts of feeding ratios (see table 1) were dissolved in 11.3 g of mixed solvents with 7 to 3 compositions of ethyl lactate (EL) and gamma butyrolactone (GBL) in round-bottom flask A. A 0.51 g of dimethyl-2,2'-azobis-2-methylpropionate (V-601 azo initiator from Wako Specialty Chemicals) was dissolved in 1.8 g of mixed EL and GBL solution in round-bottom flask B. A 10.8 g of mixed EL and BLS solution was charged on 50 ml of two-neck round-bottom flask C. This solvent in flask C was purged with N2 gas and heated to 80° C. with gently stirring. Solution in flask B was added to solution in flask A slowly. This mixed solution was added dropwise to flask C during 90 minutes by using a syringe pump and then stirred for 4 h. Reaction mixture was cooled to room temperature and 337 g of solvent mixture of MeOH and $H_2O$ as 9 to 1 of weight percentage. Final precipitate was filtered and dried for 16 hours to obtain target polymer.

Example 9: Synthesis of MMCHMA/aGBLMA/X-GM-HL2/HAMA

A 2.81 g of MMCHMA, 1.69 g of aGBLMA, 0.71 g of MHLMA, 1.80 g of HAMA were used. Target polymer was synthesized by using general polymerization procedures. Total yield of target polymer was 51% (3.6 g) with 11,800 of Mw, 1.45 of PDI, and 125.4° C. of glass transition temperature.

Example 10: Synthesis of ECHMA/aGBLMA/X-GM-HL2/HAMA

A 2.91 g of EMCHMA, 1.64 g of aGBLMA, 0.69 g of MHLMA, 1.75 g of HAMA were used. Target polymer was synthesized by using general polymerization procedures. Total yield of target polymer was 49% (3.4 g) with 10,000 of Mw, 1.39 of PDI, and 135.2° C. of glass transition temperature.

Example 11: Synthesis of EMCHMA/aGBLMA/X-GM-HL2/HAMA

A 2.66 g of ECHMA, 1.74 g of aGBLMA, 0.74 g of MNLMA, 1.48 g of HAMA were used. Target polymer was synthesized by using general polymerization procedures. Total yield of target polymer was 58% (5.8 g) with 9,900 of Mw, and 1.47 of PDI.

Examples 12-15: Photoresist Composition Preparation

General procedure of photoresist preparation for PTD (positive-tone development) application A 38.85 g of polymer solution (15% in PGMEA), 31.04 g of 1-(4-(tert-butyl)phenyl)tetrahydro-1H-thiophen-1-ium 2-(2-(((1S,2R,4R)-bicyclo[2.2.1]heptan-2-yl)-1,1,2,2-tetrafluoroethoxy)-1,1,2,2-tetrafluoroethane-1-sulfonate solution (2% in methyl-2-hydroxyisobutyrate), 5.03 g of tert-butyl (1,3-dihydroxy-2-(hydroxymethyl)propan-2-yl) carbamate solution (1% in methyl-2-hydroxyisobutyrate), 0.85 g of polymer (GAM-DFPA/ECPMA) solution (23.6%

TABLE 1

Feeding ratios of a series of monomers for polymer synthesis

| No of Examples | MCHMA | ECHMA | MMCHMA | EMCHMA | aGBLMA | MNLMA | HAMA |
|---|---|---|---|---|---|---|---|
| 8 | 40 | — | — | — | 30 | 7 | 23 |
| 9 | — | — | 40 | — | 30 | 7 | 23 |
| 10 | — | 40 | — | — | 30 | 7 | 23 |
| 11 | — | — | — | 40 | 30 | 7 | 23 |

(MMCHMA, EMCHMA, MCHMA, and ECHMA in Table 1 were prepared by using synthetic procedure of example 1 to 4. aGBLMA (2-methyl-acrylic acid 2-oxo-tetrahydro-furan-3-yl methacrylate), HAMA (3-hydroxy-adamantyl methacrylate), and MHLMA (2-oxo-2-(((1R,6S,8S)-5-oxo-4-oxatricyclo[4.3.1.13,8]undecan-2-yl)oxy)ethyl methacrylate) are commercially available.)

Example 8: Synthesis of MCHMA/aGBLMA/X-GM-HL2/HAMA

A 3.65 g of MCHMA, 2.55 g of aGBLMA, 1.08 g of MHLMA, 2.72 g of HAMA were used. (Target polymer was synthesized by using general polymerization procedures. Total yield of target polymer was 76% (7.61 g) with 8,600 of Mw, 1.57 of PDI, and 131.4° C. of glass transition temperature.

in PGMEA), 17.64 g of PGMEA and 6.59 g of methyl-2-hydroxyisobutyrate were mixed and filtered with a nylon filter.

Example 11: Photoresist 1 was Prepared by Admixing the Polymer Prepared in Example 8

Photoresist 1 was prepared by using the polymer which was prepared in Example 8 with general procedure of photoresist preparation.

Example 12: Photoresist 2 was Prepared by Admixing the Polymer Prepared in Example 9

Photoresist 2 was prepared by using the polymer which was prepared in Example 9 with general procedure of photoresist preparation.

Example 13: Photoresist 3 was Prepared by Admixing the Polymer Prepared in Example 10

Photoresist 3 was prepared by using the polymer which was prepared in Example 10 with general procedure of photoresist preparation.

Example 14: Photoresist 4 was Prepared by Admixing the Polymer Prepared in Example 11

Photoresist 4 was prepared by using the polymer which was prepared in Example 11 with general procedure of photoresist preparation.

Example 15: Lithographic Processing and Performances

For the immersion lithographic test, resist and underlying antireflective coating (BARC) and baking were performed with Lithius Track (TEL, Tokyo Electron Co.) with 300 mm silicon wafers. Exposure was carried out with Nikon S610C immersion 193 nm scanner. An exposed wafer was developed in 2.38% of tetra methyl ammonium hydroxide (TMAH) by using Lithius.

Lithographic processing conditions are set forth in Table 5 below. Substrate condition is dual BARCs (BARC B with 230 Å on BARC A with 540A) with a minimum reflectivity. The photoresistresist film thickness was 2200 Å at the soft bake temperature (SB) of 100° C. Post Exposure Bake (PEB) was 100° C. The illumination condition is 0.93 NA and annular with 0.8 outer and 0.51 inner sigma. Phase Shift Mask (PSM) was used with the mask pattern of 72.5 nm line and 160 nm pitch for dense line, 110 nm line and 700 nm pitch for isolated line and 100 nm space and 700 nm pitch for isolated trench. Target CD is 80 nm line for dense line and 90 nm line for isolated line and 90 nm space for isolated trench.

TABLE 5

| Lithographic process conditions | |
|---|---|
| Process conditions | |
| Substrate | 300 mm Silicon |
| | 1st layer: BARC A, Film Thickness: 540 A, Bake temperature: 205 C. |
| | 2nd layer: BARC B, Film Thickness: 230 A, Bake temperature: 205 C. |
| MASK | 6% Phase Shift Mask (PSM) |
| Illumination | 0.93 NA, Annular outer sigma 0.8/inner sigma 0.51 |
| Film Thickness | 2200 A |
| Softbake | 100° C./60 seconds |
| Post exposure bake | 100° C./60 seconds |
| MASK Feature | Dense Line: 72.5 nm Line and 160 nm Pitch |
| | Isolated Line: 110 nm Line and 700 nm Pitch |
| | Isolated Trench: 100 nm Space and 700 nm Pitch |
| Target CD | Dense Line: 80 nm Line |
| | Isolated Line: 90 nm Line |
| | Isolated Trench: 90 nm Space |

Litho Performance for New Ether Leaving Groups

MMCHMA was compared with MCHMA and EMCHMA was also compared with ECHMA for litho performance in Table 5. MMCHMA as a more polar leaving group shows more sloped profile at dense line and isolated trench pattern than MCHMA. EMCHMA also shows similar trend when it compared with ECHMA. It looks this sloped profile affects to EL and DoF margin and LWR. Ether leaving groups (MMCHMA and EMCHMA) show worse EL and DoF margin and LWR than controls (MCPMA and ECHMA). Since ether leaving groups expect to dissolve faster than controls due to more hydrophilic property and lower Tg, the photo speed (Eop: Optimum Energy) of them has faster than controls. The interesting point is that polar leaving groups have much faster Eop at the isolated line than controls. It means that the Eop bias between isolated line and dense line is smaller. It seems the polymer with polar leaving group is much easier to be deblocked and developed in TMAH solution at the isolated line with relatively rich acid concentration than at the dense line and isolated trench and it makes smaller isolated line CD.

Example 16: Preparation of Photoresist 5 for NTD Application

A 17.44 g of polymer (IPAMA/IPCPMA/aGBLMA/X-GM-HL-2) solution (15% in PGMEA), 38.75 g of triphenylsulfonium 4-(((3r,5r,7r)-adamantane-1-carbonyl)oxy)-1,1,2,2-tetrafluorobutane-1-sulfonate (full name) solution (1% in methyl-2-hydroxyisobutyrate), 4.58 g of (4-(tert-butyl)phenyl)diphenylsulfonium ((3s,5s,7s)-adamantan-1-yl)sulfamate (full name) solution (2% in methyl-2-hydroxyisobutyrate), 1.99 g of trioctylamine (full name) solution (1% in PGMEA), 1.24 g of 1-butyl 5-isobutyl 2,2,4,4-tetramethylpentanedioate polymer (5% in PGMEA), 20.78 g of PGMEA, 9.69 g of gamma-butyrolactone and 5.52 g of methyl-2-hydroxyisobutyrate were mixed and filtered with a nylon filter.

Example 17.—Preparation of Photoresist 6 for NTD Application

A 17.44 g of polymer (MMCHMA/IPAMA/IPCPMA/aGBLMA/X-GM-HL-2) solution (15% in PGMEA), 38.75 g of triphenylsulfonium 4-(((3r,5r,7r)-adamantane-1-carbonyl)oxy)-1,1,2,2-tetrafluorobutane-1-sulfonate solution (1% in methyl-2-hydroxyisobutyrate), 4.58 g of (4-(tert-butyl)phenyl)diphenylsulfonium ((3s,5s,7s)-adamantan-1-yl)sulfamate solution (2% in methyl-2-hydroxyisobutyrate), 1.99 g of trioctylamine solution (1% in PGMEA), 1.24 g of 1-butyl 5-isobutyl 2,2,4,4-tetramethylpentanedioate polymer solution (5% in PGMEA), 20.78 g of PGMEA, 9.69 g of gamma-butyrolactone and 5.52 g of methyl-2-hydroxyisobutyrate were mixed and filtered with a nylon filter.

Example 18. Lithographic Performance for NTD Application

A 300 mm HMDS-primed silicon wafers were spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C., providing the first BARC layer thickness of 900 Å.

The fabricated films were then exposed through a mask on Nikon S306C ArF immersion scanner using the illumination conditions as follows: 1.3 NA, Annular with XY-polarization, δ0.64-0.8. The exposure dose was varied from 23.0 mJ/cm$^2$ to 47.0 mJ/cm$^2$ by 1 mJ/cm$^2$. The exposed film was then post-exposure baked at 90° C. for 60 seconds, followed by the developing with n-butyl acetate for 18 seconds using a TEL CLEAN TRAC LITHIUS i+, which provides the patterns with negative tone development. Critical dimensions (CDs) of the pattern of 44 nm 126 pitch Trench, bright field phase-shifted by 180° with transmittance 0.06) were measured on a Hitachi CG4000 CD SEM.

What is claimed is:

1. A polymer comprising a repeat unit that comprises a structure corresponding to the following Formulae (I) or (I'):

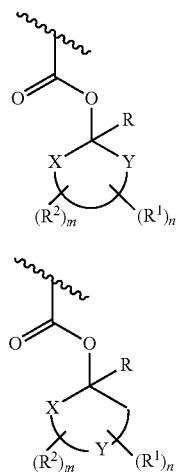

wherein in each of Formulae (I) and (I'):
X and Y are independently C, O, or S and form a carbon alicyclic ring or heteroalicyclic ring;
R is a non-hydrogen substituent; $R^1$ is optionally substituted ether or optionally substituted thioether;
$R^2$ is a non-hydrogen substituent;
m is an integer an integer of 0 or greater;
n is a positive integer; and the sum of m and n do not exceed the available valances of the carbon alicyclic ring or heteroalicyclic ring.

2. A polymer of claim 1 wherein the polymer comprises a repeat unit that comprises a structure corresponding to the following Formula (II):

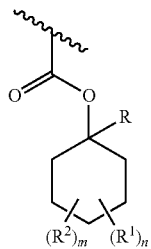

wherein in Formula (II):
R is a non-hydrogen substituent;
$R^1$ is optionally substituted ether or optionally substituted thioether;
$R^2$ is a non-hydrogen substituent;
m is an integer an integer of 0 (where no $R^2$ groups are present) or greater;

n is a positive integer; and the sum of m and n do not exceed the available valances of the carbon alicyclic ring.

3. The polymer of claim 1 wherein m is zero.
4. The polymer of claim 1 wherein $R^1$ is present as a 4-position substituent.
5. The polymer of claim 2 wherein $R^1$ is present as a 4-position substituent.
6. The polymer of claim 3 wherein n is 1.
7. The polymer of claim 4 wherein n is 1.
8. The polymer of claim 1 wherein the polymer comprises a repeat unit that comprises a structure corresponding to Formula (I).
9. The polymer of claim 1 wherein the polymer comprises a repeat unit that comprises a structure corresponding to Formula (I').
10. A polymer that comprises a unit provided by one or more of the following:

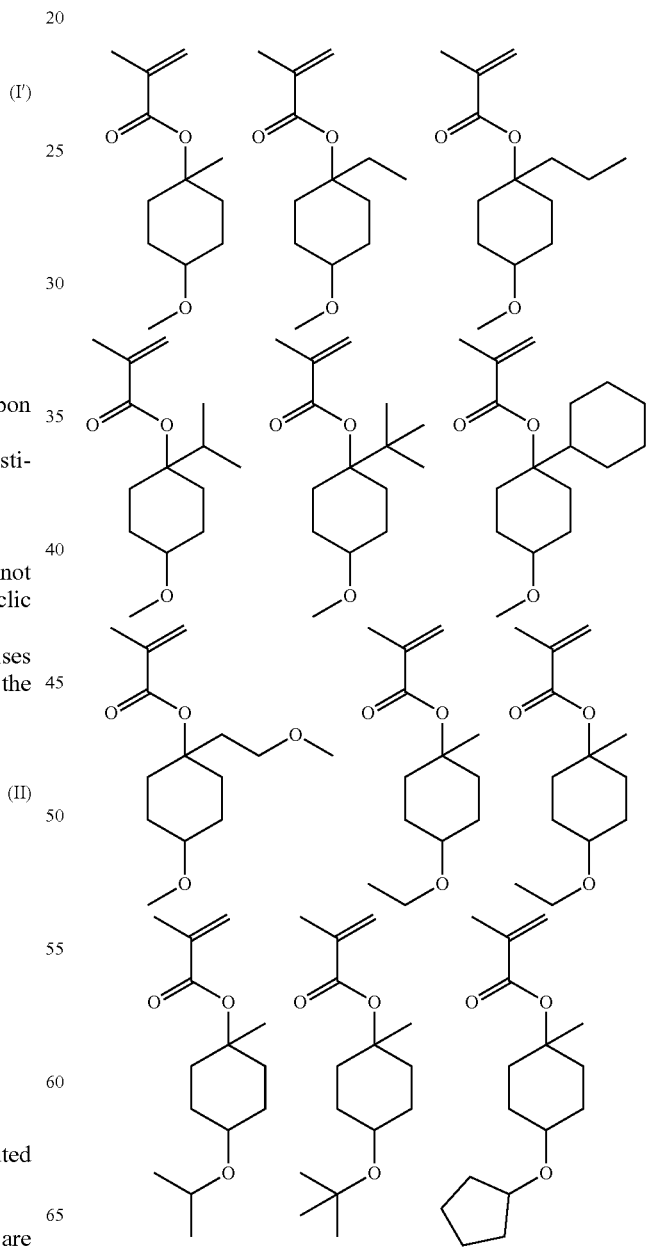

37
-continued
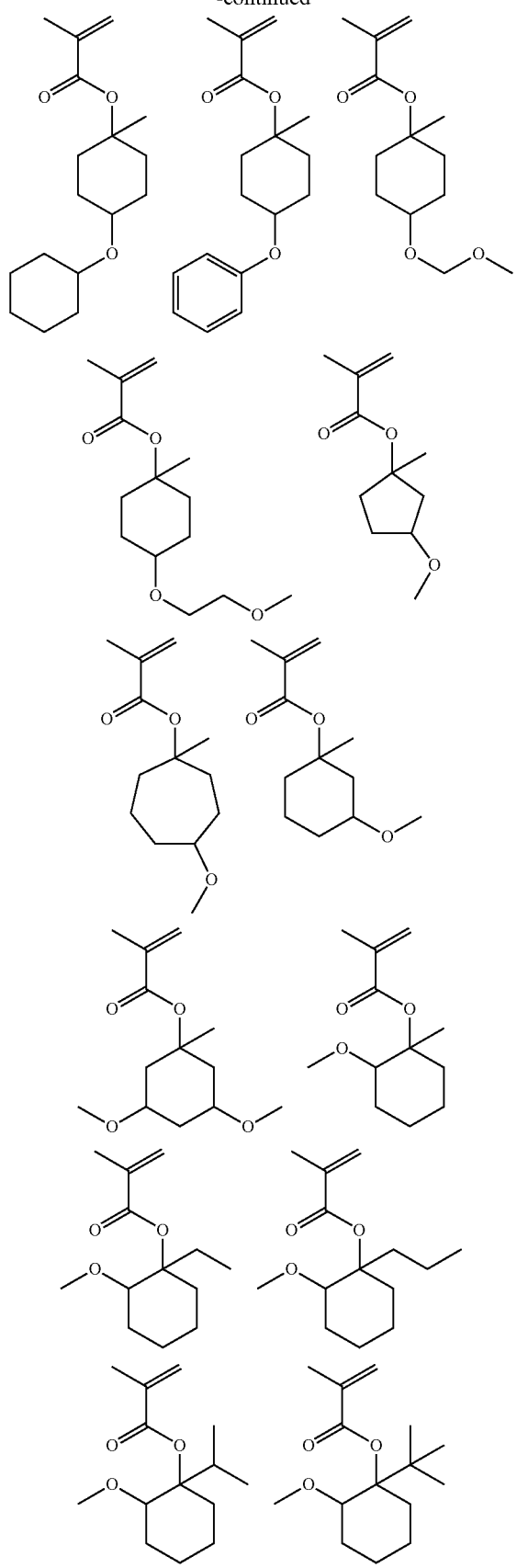
38
-continued
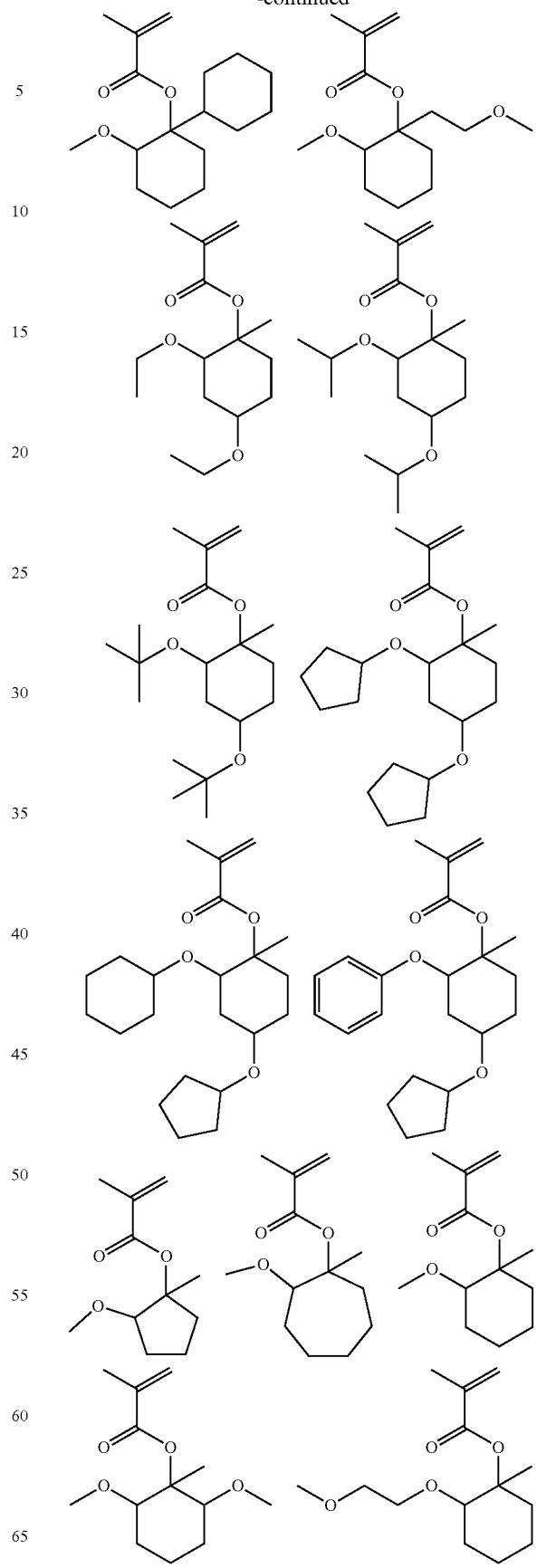

-continued
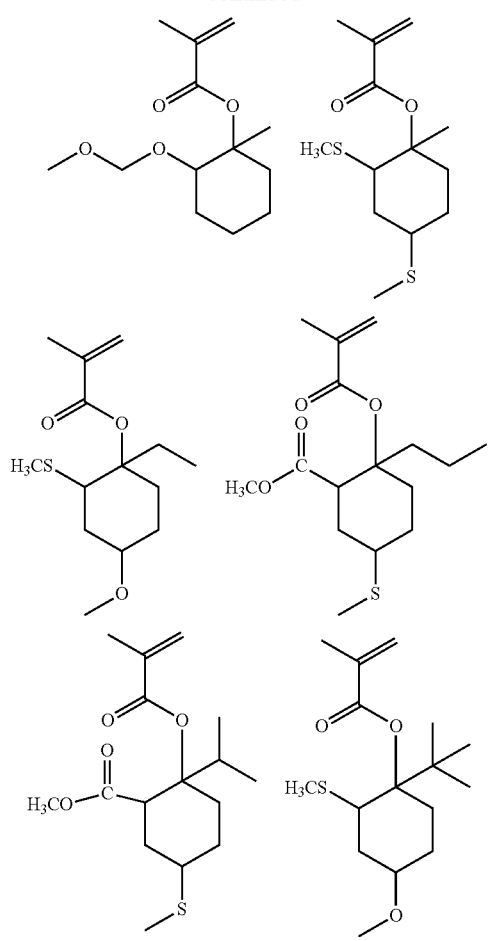
-continued
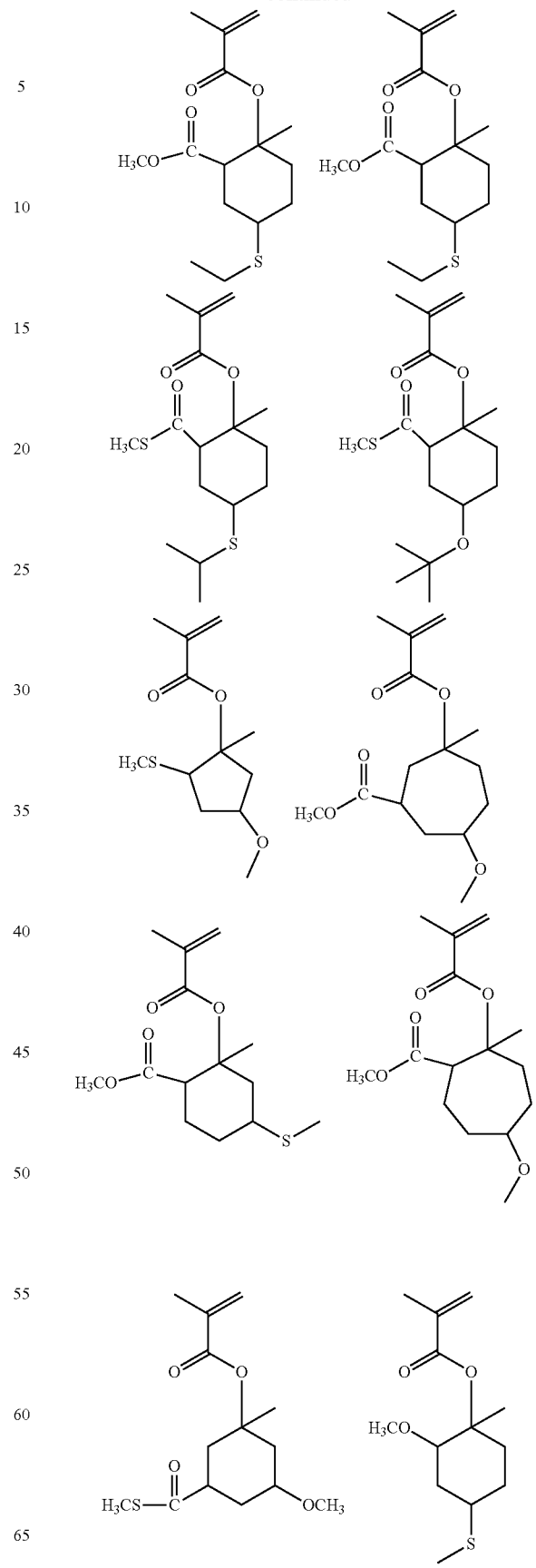

-continued

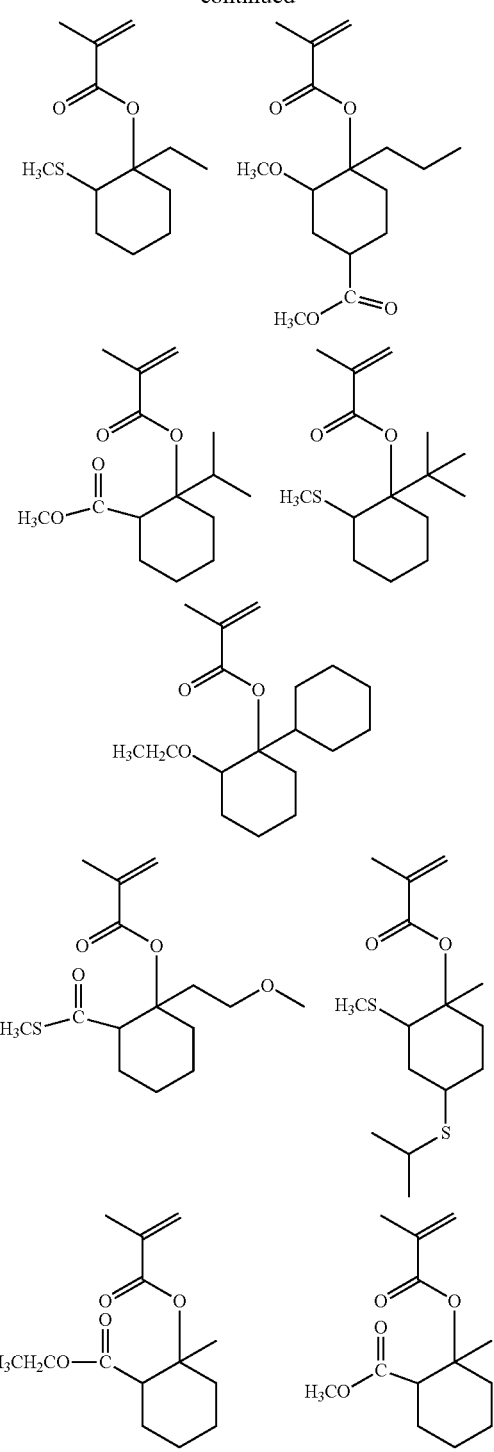

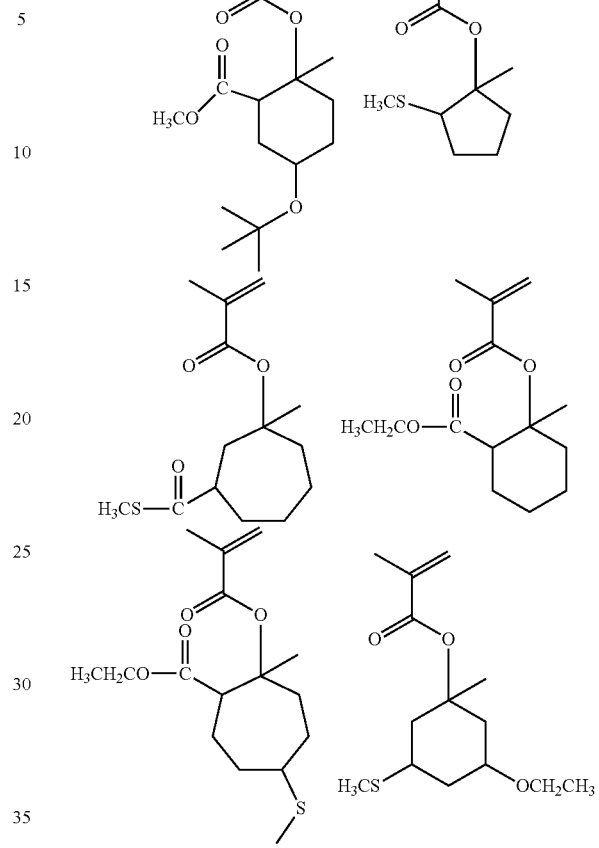

11. A photoresist composition comprising a photoactive component and a polymer of claim 1.
12. A photoresist composition comprising a photoactive component and a polymer of claim 2.
13. A photoresist composition comprising a photoactive component and a polymer of claim 3.
14. A photoresist composition comprising a photoactive component and a polymer of claim 4.
15. A photoresist composition comprising a photoactive component and a polymer of claim 5.
16. A photoresist composition comprising a photoactive component and a polymer of claim 6.
17. A photoresist composition comprising a photoactive component and a polymer of claim 7.
18. A photoresist composition comprising a photoactive component and a polymer of claim 8.
19. A photoresist composition comprising a photoactive component and a polymer of claim 9.
20. A photoresist composition comprising a photoactive component and a polymer of claim 10.

* * * * *